US006318647B1

(12) United States Patent
Gaw et al.

(10) Patent No.: US 6,318,647 B1
(45) **Date of Patent: *Nov. 20, 2001**

(54) DISPOSABLE CARTRIDGE FOR USE IN A HAND-HELD ELECTROSTATIC SPRAYER APPARATUS

(75) Inventors: Chinto Benjamin Gaw, Cincinnati; Chow-Chi Huang, West Chester; Ayub Ibrahim Khan, Cincinnati, all of OH (US); Ivan Andrew McCracken, Edinboro, PA (US); Eric Jason Wallace, Cincinnati; Robert James Peterson, Loveland, both of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/377,332

(22) Filed: Aug. 18, 1999

(51) Int. Cl.$^7$ .......... B05B 5/00

(52) U.S. Cl. .......... 239/690; 239/691; 239/692; 239/704; 239/706; 239/708

(58) Field of Search .......... 239/690, 691, 239/692, 704, 706, 708

(56) References Cited

U.S. PATENT DOCUMENTS

| | | | | |
|---|---|---|---|---|
| 2,159,894 | | 5/1939 | Hines | 299/89 |
| 2,629,516 | | 2/1953 | Badham | 222/79 |
| 3,012,969 | | 12/1961 | van der Minne | 252/153 |
| 3,495,779 | * | 2/1970 | Renner et al. | 239/691 |
| 3,711,022 | * | 1/1973 | Witte | 239/708 |

(List continued on next page.)

FOREIGN PATENT DOCUMENTS

| | | | | |
|---|---|---|---|---|
| 868443 | | 12/1978 | (BE) . | |
| 882449 | | 7/1980 | (BE) . | |
| 882450 | | 7/1980 | (BE) . | |
| 096 731 A1 | | 12/1983 | (EP) . | |
| B1120633 | | 7/1984 | (EP) . | |
| 523 960 A1 | | 1/1993 | (EP) . | |
| 523 961 A1 | | 1/1993 | (EP) . | |
| 523 962 A1 | | 1/1993 | (EP) . | |
| 523 963 A1 | | 1/1993 | (EP) . | |
| 523 964 A1 | | 1/1993 | (EP) . | |
| 544 158 | | 6/1993 | (EP) . | |
| 2127433 | | 9/1972 | (FR) . | |
| 2 128 900 A | | 5/1984 | (GB) . | |
| 2 273 673A | | 6/1994 | (GB) . | |
| 2 273 872 A | | 7/1994 | (GB) . | |
| 2153260 | * | 8/1985 | (GB) | 239/690 X |
| 282-67347 | | 6/1998 | (JP) . | |
| 867927 | | 9/1981 | (SU) . | |
| WO 94/11119 | | 5/1994 | (WO) . | |
| WO 94/27560 | | 12/1994 | (WO) . | |
| WO 95/29758 | | 11/1995 | (WO) . | |
| WO 96/10459 | | 4/1996 | (WO) . | |
| WO 96/11062 | | 4/1996 | (WO) . | |
| WO 97/33527 | | 9/1997 | (WO) . | |
| 96/40441 | | 12/1996 | (WO) | B05B/5/025 |
| 98/18561 | | 5/1998 | (WO) | B05B/5/025 |

*Primary Examiner*—Robin O. Evans
(74) *Attorney, Agent, or Firm*—Jack L. Oney, Jr.

(57) ABSTRACT

A disposable catridge for use with an electrostatic charging device. The disposable cartridge can have a reservoir configured to contain a supply of product suitable for electrostatic spraying, a nozzle configured and disposed to disperse the electrostatically charged product, and an electrode disposed to electrostatically charge the product prior to its dispersal. The disposable cartridge can also have an insulator for insulating the supply of product from electrostatic charge.

19 Claims, 20 Drawing Sheets

U.S. PATENT DOCUMENTS

| | | | | |
|---|---|---|---|---|
| 4,079,894 | | 3/1978 | Harjar et al. | 239/526 |
| 4,122,845 | | 10/1978 | Stouffer et al. | 128/66 |
| 4,143,819 | | 3/1979 | Hastings | 239/707 |
| 4,194,696 | | 3/1980 | Harjar | 239/707 |
| 4,258,073 | | 3/1981 | Payne | 427/1 |
| 4,324,361 | * | 4/1982 | Moos et al. | 239/706 X |
| 4,380,786 | * | 4/1983 | Kelly | 239/690 X |
| 4,398,671 | * | 8/1983 | Coffee | 239/690 |
| 4,561,037 | | 12/1985 | MacLaine et al. | 361/228 |
| 4,577,803 | | 3/1986 | Owen | 239/690 |
| 4,907,727 | | 3/1990 | Ernst et al. | 222/386.5 |
| 5,105,984 | | 4/1992 | Kazimir | 222/103 |
| 5,221,050 | | 6/1993 | Jeffries et al. | 239/708 |
| 5,222,663 | | 6/1993 | Noakes et al. | 239/3 |
| 5,229,105 | | 7/1993 | Wilmsmann | 424/59 |
| 5,268,166 | | 12/1993 | Barnett et al. | 424/47 |
| 5,292,067 | | 3/1994 | Jeffries et al. | 239/3 |
| 5,296,681 | | 3/1994 | Tschuder | 219/410 |
| 5,322,684 | | 6/1994 | Barnett et al. | 424/47 |
| 5,405,090 | | 4/1995 | Greene et al. | 239/708 |
| 5,422,630 | | 6/1995 | Quinn et al. | 340/661 |
| 5,468,488 | | 11/1995 | Wahl | 424/78.03 |
| 5,490,633 | | 2/1996 | Jeffries et al. | 239/691 |
| 5,494,674 | | 2/1996 | Barnett et al. | 424/401 |
| 5,519,159 | | 5/1996 | Narabe et al. | 558/169 |
| 5,662,890 | | 9/1997 | Punto et al. | 424/59 |
| 5,674,481 | | 10/1997 | Wahl | 424/78.03 |
| 5,732,884 | | 3/1998 | Jauner | 239/288.3 |
| 6,079,634 | * | 6/2000 | Noakes et al. | 239/690 X |

* cited by examiner

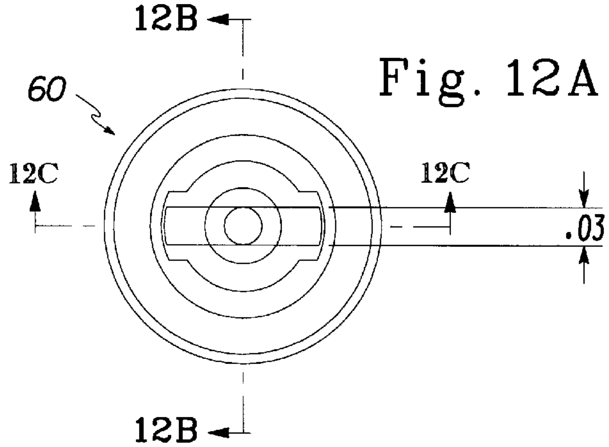
Fig. 12A
Fig. 12B
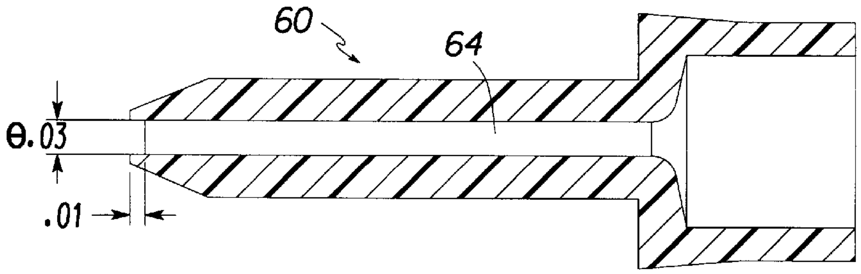
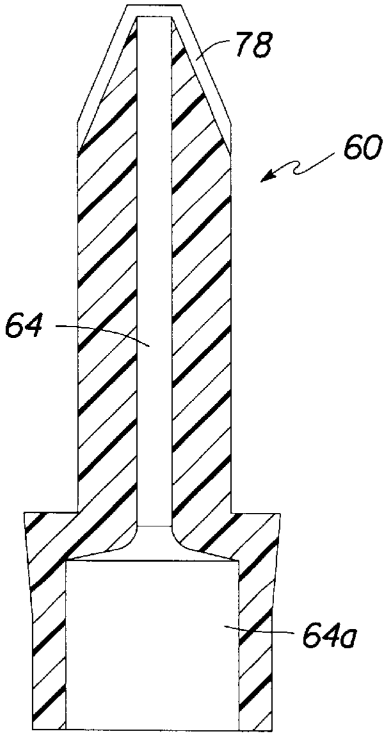
Fig. 12C
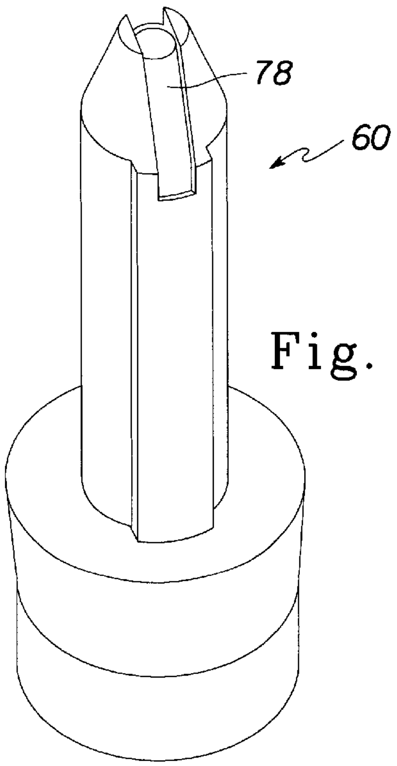
Fig. 12D

DISPOSABLE CARTRIDGE FOR USE IN A HAND-HELD ELECTROSTATIC SPRAYER APPARATUS

BACKGROUND OF THE INVENTION

1. Field of the Invention

This invention relates to cartridges for electrostatic spraying apparatus, and more specifically to disposable cartridges for use in electrostatic spraying apparatus for cosmetic products.

2. Background Information

Traditionally most skin care or cosmetic products, such as lotions, perfumes, and make-up, for example, have been applied by a limited number of methods. For example, frequently they are simply applied by the hand of the user, who would spread or rub the product onto the skin with the fingers or with the aid of an application pad. These produces are also frequently sold in pump sprays or pre-pressurized aerosol containers, so as to have the product atomized and sprayed with the aid of a propellant gas.

More recently, electrostatic spraying devices have been developed for the application of personal care products, such as skin care and cosmetic products. However, many of these more recent apparatus can still be bulky and/or require bench top equipment and external electrical wiring, which can make them cumbersome or hard to use. A few portable hand-held electrostatic devices are also known, however these known electrostatic devices frequently require the product to be dispersed by the application of pressure by hand, or from a pre-pressurized container, with the aid of a propellant, such as a fluorocarbon, or chlorofluorocarbon, for example. Additionally, many known electrostatic spraying devices require the pouring of the product into a separate refillable container, which container is then connected to the spraying device by a hose or a dip tube.

Typically, the known application methods and apparatus have a number of drawbacks. For example, frequently these methods and devices are unable to deliver a desired target product flow rate with great accuracy and precision, thus resulting in uneven coverage and wasted product. These drawbacks can be particularly troublesome when applying cosmetics, such as foundation, for example. Applying too much foundation in an uneven manner can result in both excessive wasted amounts of potentially expensive cosmetics, as well as an unsatisfactory and unattractive final appearance of the skin to which the foundation is applied. For example, when all the skin is covered the natural skin tones cannot show through, and the user can feel like she is wearing a mask. Consequently, known application processes and products frequently make it difficult to adequately conceal skin flaws and yet create a finished "look" which is both natural in appearance and long lasting.

Additionally, some of the known electrostatic spraying devices do not adequately focus the electrical charge and/or insulate the product supply from the electrostatic charge. This can particularly be a problem when a two-phased product, such as a two-phased foundation, is used in the device, since some of these products can be prone to separation when electrostatic charge travels to the reservoir containing the supply of product.

Further, since many known electrostatic devices have containers or reservoirs, which continually need refilling with product, these containers can not only be inconvenient to refill, but can also be messy and thus require cleaning and maintenance by the user. Refilling can also result in a risk of contamination of the new product by residue, left in the container. Additionally, known electrostatic spraying devices typically have one spray nozzle which is repeatedly reused. After repeated and/or long-term use this single nozzle can be subject to clogging and contamination, thus also requiring maintenance and cleaning by the user. Additionally, many known nozzles are made of conductive material, which can result in the user accidentally touching the nozzle and thereby potentially shocking themselves or grounding the device.

Finally, in known electrostatic spraying devices, manufacturing problems and additional costs can result from the production of numerous separate pieces, such as separate electrodes, nozzles and insulators.

OBJECTS OF THE INVENTION

An object of the present invention is to create a hand-held, self-contained electrostatic spraying device which is easy to use.

Another object of the present invention is to create an electrostatic spraying device that provides a precise essentially constant flow rate of product, to provide uniformity and ease of application, as well as to conserve product usage.

Another object of the present invention is to provide a disposable cartridge to be used in the electrostatic spraying device, which disposable cartridge is configured to hold a supply of product suitable for electrostatic spraying, and is easy and convenient to use.

Another object of the present invention is to create an electrostatic spraying device that permits the application of a cosmetic foundation product in substantially uniformly spaced droplets so as to create a desirable appearance or "look" for foundation users, such that the foundation conceals skin flaws, yet appears natural.

Another object of the present invention is to create a hand-held, self-contained electrostatic spraying device which is easy to use which eliminates the need for bench top, equipment and external electrical wiring.

Another object of the present invention is to provide a disposable cartridge with a nozzle made from a non-conductive material which thus minimizes accidental shocking and/or grounding of the device by the unintentional touching of the nozzle.

Another object of the present invention is to provide a disposable cartridge which has the spray nozzle as part of the cartridge, such that the nozzle is replaced each time a new cartridge is inserted into the spraying device, thereby essentially obviating the need to clean the nozzle.

Another object of the present invention is to provide a non-refillable disposable cartridge containing a supply of product suitable for electrostatic spraying, such that a separate refillable external product supply container is not required for the electrostatic spraying device.

Another object of the present invention is to reduce manufacturing problems and/or costs by providing a disposable cartridge in which the nozzle, insulator and electrode can be manufactured as one integral part.

Another object of the present invention is to provide a disposable cartridge which adequately focuses the electrostatic charge and insulates the product supply such that two-phase product separation is minimized.

SUMMARY OF THE INVENTION

These objects can be achieved by an electrostatic spraying device which is designed to be a hand-held, self-contained, battery operated electrostatic spraying device, with a disposable cartridge.

The electrostatic spraying device can comprise a housing configured to be held by the hand of a user, a disposable cartridge configured to contain a supply of product, such as a cosmetic product, and a nozzle for spraying the product onto the skin of the recipient. An electrode for electrostatically charging the product can be disposed to charge the product prior to its dispersal. The device can also be configured for moving the product from the supply of product, past the electrode, and to a dispersal point. A self-contained power supply arrangement can also be disposed within the housing to provide electrical power for the device.

The electrostatic spraying device is preferably designed in size and weight to be easily held and operated by the hand of the user. Further, the device is preferably self-contained such that essentially all of necessary components, such as the product supply and power supply, can be contained within the housing of the device. Therefore, preferably no external, potentially bulky or cumbersome, sources for product or power are required. This permits the electrostatic spraying device to be portable, since it can be used in virtually any location, and can be easily transported by the user from one location to another.

The housing of the device can include a gripping area substantially contoured to the shape of a users hand. This gripping area can be contoured such that the device can be easily used by an individual applying product to him- or herself, or by an individual applying product to another person, such as in a salon setting, for example.

In at least one preferred embodiment the disposable cartridge can contain a reservoir configured to contain the supply of product to be electrostatically sprayed. The disposable cartridge can be designed to be removed by the user from the electrostatic spraying device, and discarded upon depletion of the product therein. A new cartridge can then be inserted into the device to refill the product supply.

In one embodiment, the nozzle from which the product is dispersed can also be a part of the disposable cartridge. By having the nozzle as part of the disposable cartridge, a new clean nozzle is provided every time the cartridge is replaced, thereby resulting in less clogging of the nozzle, and thus necessitating less or no cleaning of the nozzle by the user. The electrode which charges the product can also be part of the disposable cartridge.

The disposable cartridge can also include an insulator for insulating the supply of product from electrostatic charge. In one embodiment, the nozzle, the electrode and the insulator can together forming a single integrated part. This single part can be formed, for example, by two shot molding.

The electrostatic spraying device can also have a motor arrangement having a speed in the range 1.1 to 6.6 revolutions per minute. In one embodiment of the electrostatic spraying device, the device can have two speed settings, thus, for example, providing a product dispensing rate from about 0.05 milliliters of product per minute to about 0.3 milliliters of product per minute.

In one embodiment, apparatus for moving the product from the product supply to a point of dispersal can include a motor and a gearbox, with a driver configured to engage with an actuator on the disposable cartridge. The cartridge can have a piston arrangement slidably mounted within its casing, connected to the actuator, wherein upon actuation of the motor, a piston is configured to pressurize the product in the casing and thereby move the product from the casing, into the nozzle, past the electrode, and then out of the electrostatic spraying device. In one embodiment, the piston can be connected to a piston rod, wherein the piston rod comprises a threaded portion having a pitch thread from about 0.016 inch to about 0.025 inch.

BRIEF DESCRIPTION OF THE DRAWING

The preferred embodiments will be discussed below with reference to the following drawings:

FIG. 12A shows a top view of one embodiment of the insulator;

FIG. 12B and 12C show cross-sectional views of the insulator embodiment shown in FIG. 12A;

FIG. 12D shows a perspective view of the insulator embodiment shown in FIG. 12A;

DESCRIPTION OF THE PREFERRED EMBODIMENTS

Figure 1:
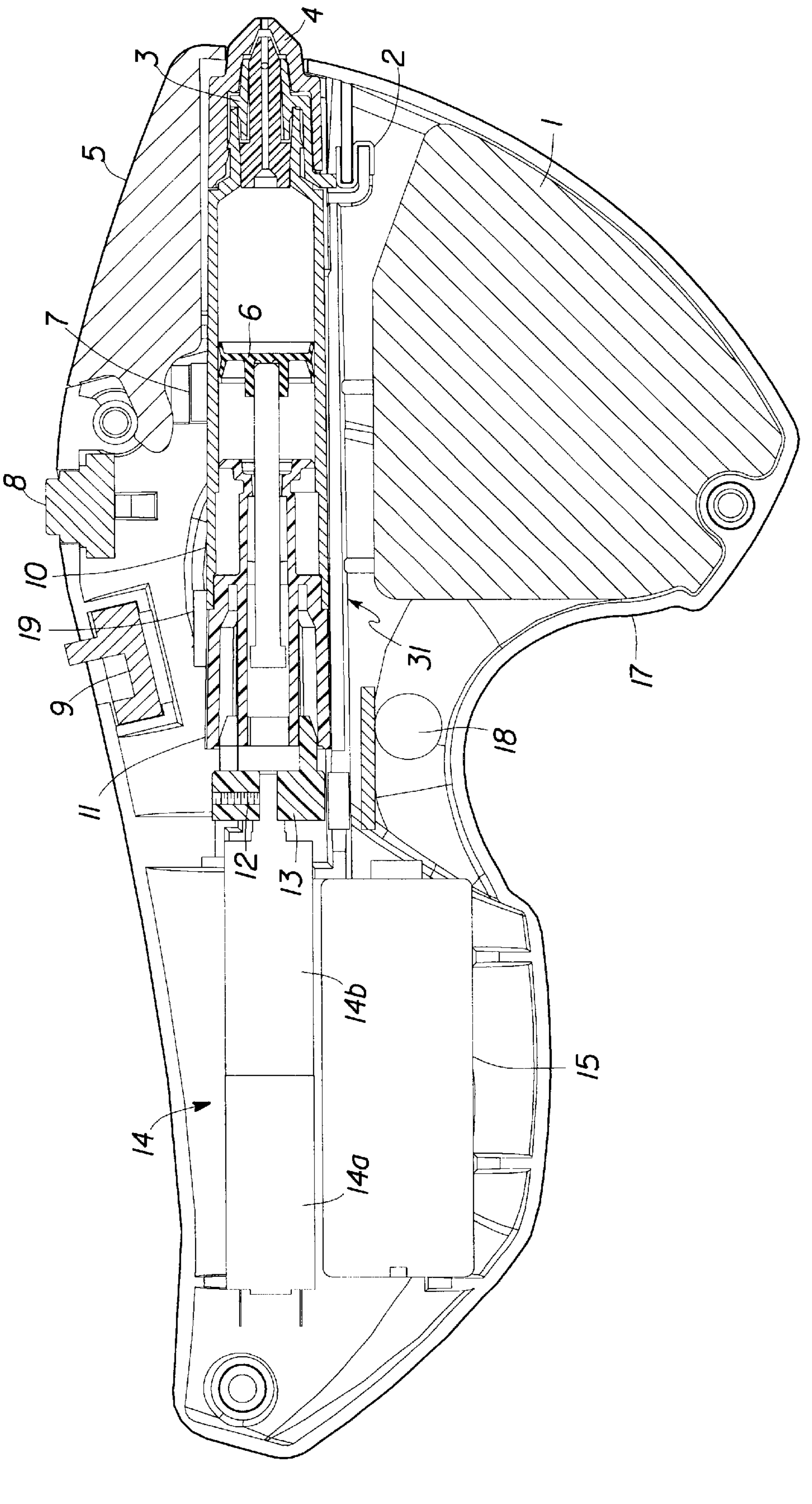
FIG. 1 shows a cross-sectional view of one embodiment of the electrostatic spraying device.
Figure 1A:
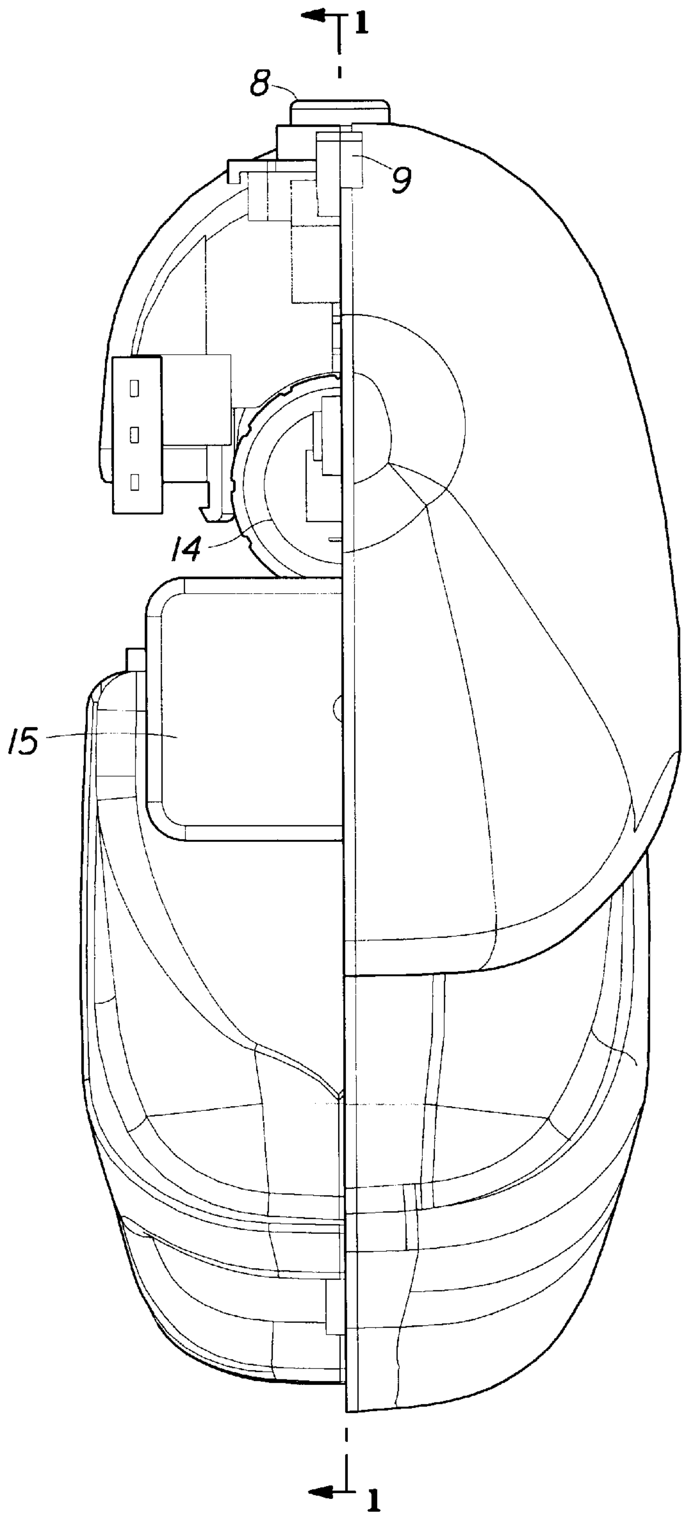
FIG. 1A, shows a split front view of the same embodiment shown in FIG. 1.

FIGS. 1 and 1A show a preferred embodiment of an electrostatic spraying device. In this embodiment the device is designed to be a hand-held, self-contained spraying device, with a disposable cartridge In brief, FIG. 1 shows a gearbox/motor component 14 which can be fixed onto a left or first housing 17. This component preferably comprises a precision motor 14*a* connected to a gearbox 14*b*. The motor/gearbox 14 can be affixed into place by either mechanical or adhesive means. Below the motor/gearbox 14 can be positioned a power supply, for example, a battery 15 is shown. Also affixed to the left housing 17 is a high-voltage power supply 1 used for charging an electrode 3 through a high voltage contacts 2, and a high voltage power supply controller circuit 18. FIG. 1 also shows an "on-off" or apply switch 8 disposed substantially on the top of the device with a motor speed selector switch 9 adjacent thereto. A disposable cartridge 31 has been inserted into the device, such that an actuator 11 of the cartridge 31, is engaged with a driver 13 attached to the motor/gearbox component 14. Additional details of the shown components are set out below. While FIG. 1 illustrates the internal components attached to the left housing 17, it is also possible to attach the components to a second or right housing 20.

Figure 2A:
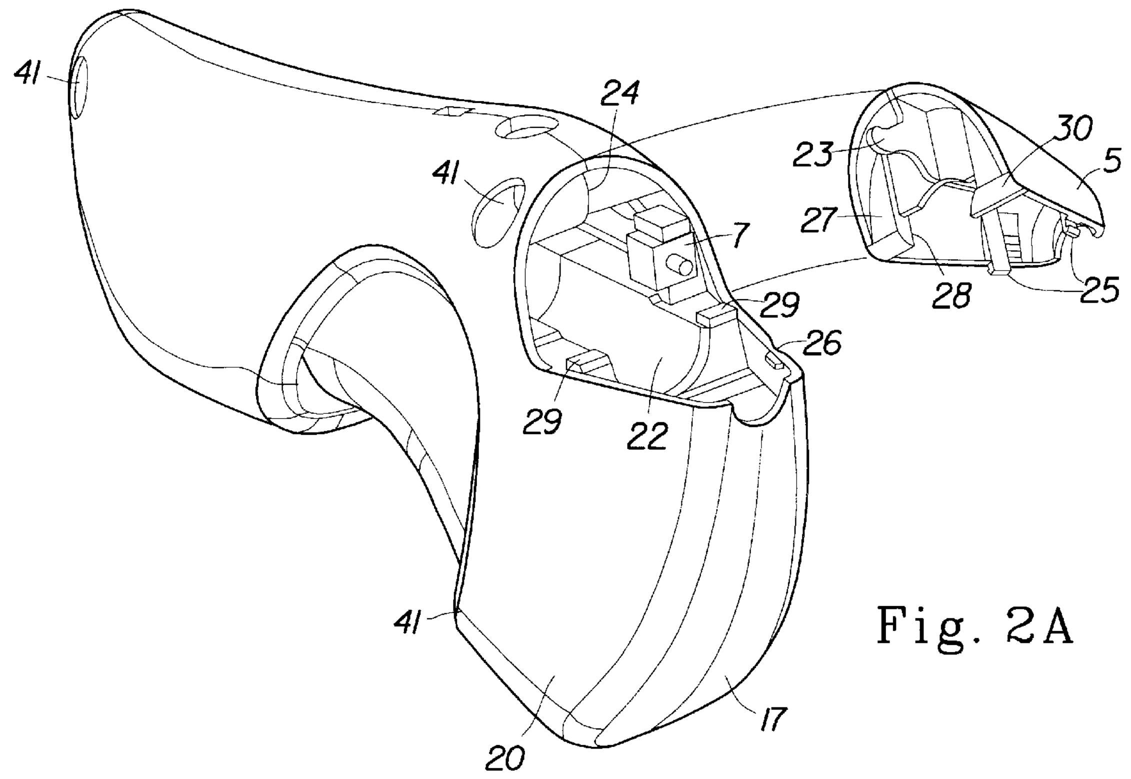
FIG. 2A shows a perspective view of the exterior of the embodiment shown in FIG. 1 with the cap removed.
Figure 2B:
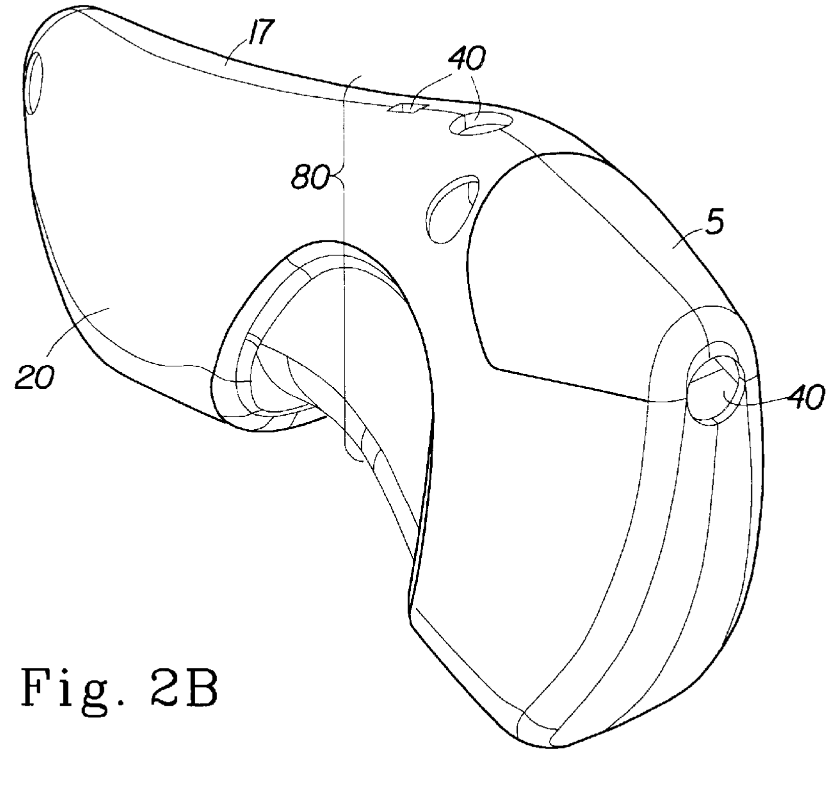
FIG. 2B shows the same embodiment as FIG. 2A, with the cap fitted on the housing.

FIGS. 2A and 2B show one possible embodiment for the housing of the inventive device. As shown, the device can have a three part housing, including a second or right housing 20, the first or left housing 17, as discussed above, and a cap portion 5, each of which can be injection molded. The housing is designed to allow an easy essentially vertical assembly of the internal component into the second housing 17. The first housing 20 can then be fastened to the second housing 17 with three screws 41 which are preferably formed from plastic. Once assembled, the two housing halves 17, 20, together form an insert-channel 22 to permit the easy insertion of the disposable cartridge 31 by a user. Once the cartridge 31 is in place, the cap 5 can be snapped onto the remainder of the housing.

The two housing halves 17, 20 are also designed to form individual openings 40 for the tip of a nozzle 4, the "on-off" or apply switch 8, and the speed selector switch 9 (see FIG. 1). This apply switch or button 8 can contain an LED indicator which indicates when the button or switch 8 is activated. One example of switch 8 could be activated, for example, by depressing. Further, a grounding circuit can be attached to, or adjacent, the apply switch 8, thereby grounding the user when the housing is grasped for activation.

To fit the cap 5 onto the rest of the housing, a circular, or curved, hook 23 on the cap 5 is first engaged with a groove 24 on the left housing 17, at about a 10–20 degree angle. The cap 5 can then be rotated down until resilient snaps 25 are deflected inward allowing them to pass over corresponding mating posts 26 on the housing, and then return to their original position. This snap-and-post arrangement secures the cap 5 tightly to the housing. The cap 5 also has a front surface 27, on a vertical rib, which is disposed to press a safety switch 7 once the cap 5 is installed on the housing, thereby completing the a electrical circuit needed to operated the device. This safety switch 7 thereby substantially prevents the accidental shocking of the user when the cap 5 is removed because the electrical circuit is broken. To essentially prevent the cap 5 from dislodging or sliding out under pressure, a back surface 28, of this same vertical rib is disposed to simultaneously press against a protrusion 29 on the housing, once the cap 5 is snapped into place. Further, the cap 5 also has horizontal ribs 30 which serve to hold-down the disposable cartridge 31 during operation of the device.

Once assembled, the housing is ergonomically designed to be easily gripped by the hand of a user. The embodiment shown in FIGS. 2A and 2B is substantially "shoe-shaped" with a narrowed center area 80 contoured to be gripped by the hand. This gripping area basically extends up and around the device such that the device can be gripped about the middle and the thumb or index finger can be conveniently and comfortably located on the apply switch 8. The housing is designed to permit the user of the device to comfortably grip the device in a variety of ways, thereby allowing the user to either apply the product to themselves or to a different recipient of the product. Therefore, the inventive electrostatic spraying device can be easily used both at home or in a salon setting. For example, one way of gripping the device can be gripping around the middle with the fingers pointing downward and wrapping around the bottom, allowing the thumb to rest on the apply switch 8. In this position the product could be easily sprayed by the user on themselves or another individual. For self application, the device can also be gripped with the nozzle 4 facing the user, and with the user's thumb being wrapped around the bottom of the gripping area 80, and the remainder of the hand being placed on top of the device, with one finger on the apply button 8. The light weight and balance of the device also allows these alternative grips. Additionally, the gripping area 80 also serves the function of positioning the hand of the user a substantial distance away from the nozzle 4, thereby substantially reducing or possibly preventing the attraction of the charged product to the hand of the user rather than to the desired area, namely, the grounded skin of the recipient. To accomplish this not only is the gripping area 80 positioned a substantial distance from the nozzle 4, but it is also recessed on the bottom portion of the device so as to allow the front of the device to also help block the hand from the nozzle 4.

Figure 3A:
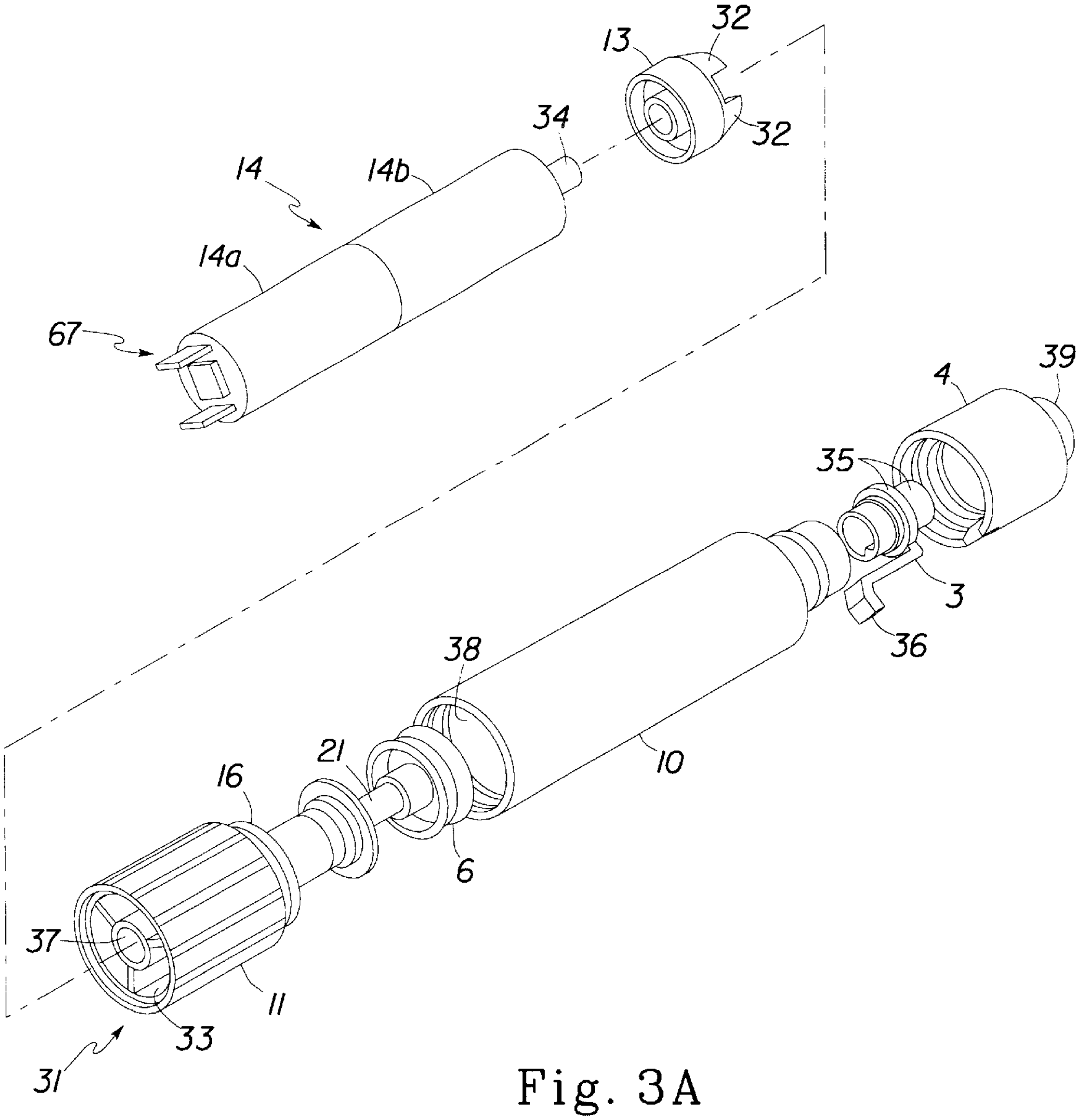
FIG. 3A shows an expanded view of one embodiment of the cartridge and the motor/gearbox component.
Figure 3B:
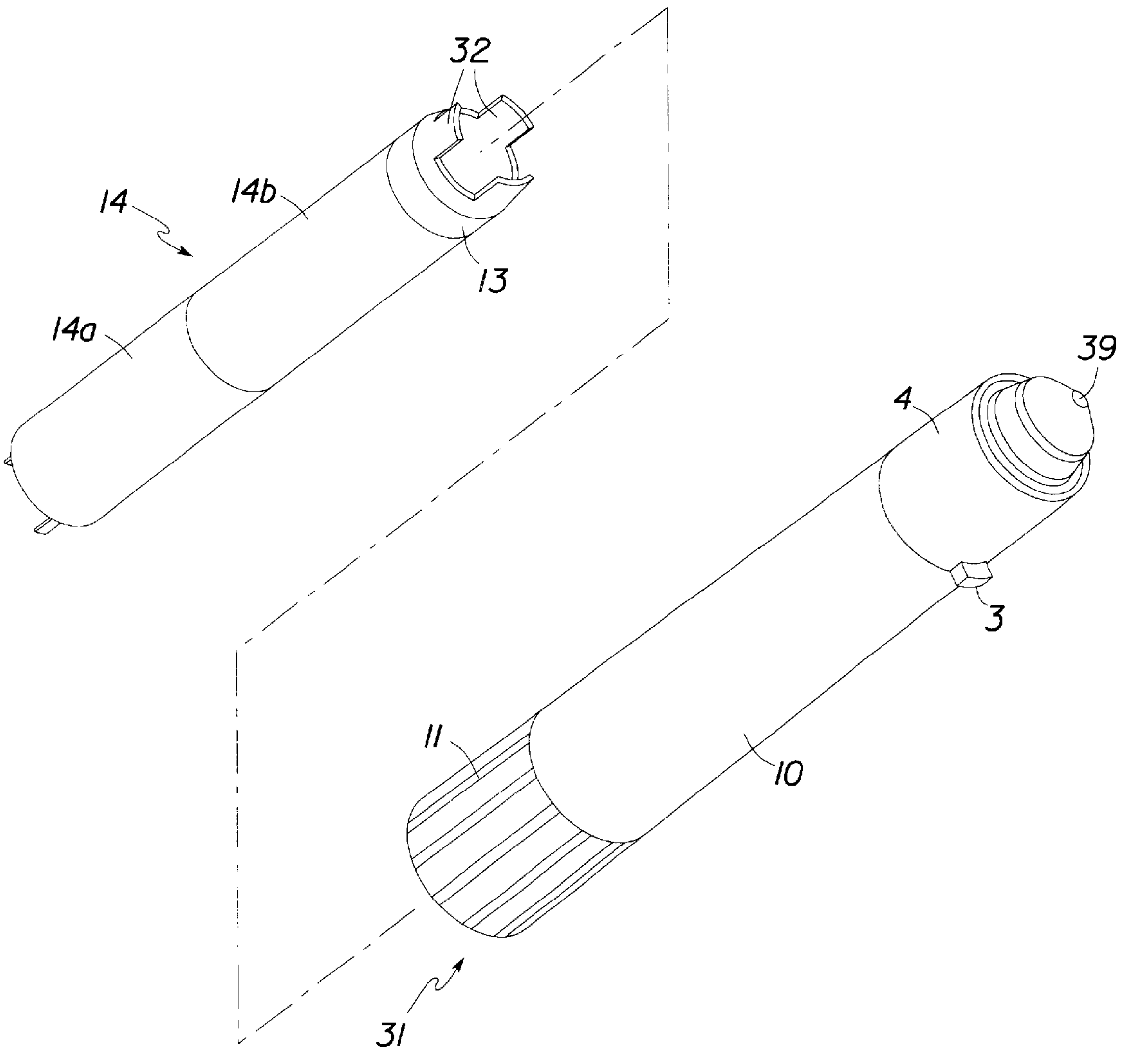
FIG. 3B shows a perspective view of the same embodiment as shown in FIG. 3A.

FIGS. 3A and 3B show one embodiment of the motor/gearbox 14 (i.e., motor 14*a* and gearbox 14*b*) and one embodiment of the disposable cartridge 31. FIG. 3A shows an, expanded view of FIG. 3B. The motor/gearbox component 14 has electrical contacts 67, including positive and negative terminals, at motor 14*a* end of the component. At the opposite end the driver 13 is fastened to a shaft 34 of gearbox 14*b*, for example, with a sent screw 12 (see FIG. 1). The driver 13 has a number of protruding fingers 32, for example, three, which can fit into matching recesses on the back 33 of an actuator 11, which actuator 11 can be part of the replaceable and disposable cartridge 31. The actuator 11 has internal threads 37 for passage of one end of a threaded shaft 21, and a snap bead 16 to snap into an open end of a casing or barrel 10 of the cartridge 31. The opposite end of the threaded shaft 21 can have a piston 6 affixed to it. The threaded shaft 21 can thereby connect the piston 6 with the actuator 11, such that the piston 6 can slide along an inner surface of the casing 10, toward a nozzle 4 of the cartridge 31, in response the turning of the actuator 11 by the motor/gearbox 14. This movement of the piston 6 can thus displace product from the cartridge 31. This positive displacement of the product can be driven, in at least one embodiment, by threaded shaft 21 having a pitch thread from about 0.016 inch to about 0.025 inch. The precision motor **14*a* and the gearbox 14*b* can have a reduction ratio of about 1024:1, and a speed in the range of about 1.1 to 6.6 revolutions per minute. In at least one embodiment the threaded shaft 21** can be formed by injection molding.

One preferred embodiment of the motor **14*a* is commercially available from Maxon Precision Motors, Inc., 838 Mitten Road, Burlingame, Calif. 94010 [Maxon DC motor RE Ø10 mm, precious metal brushes. 1.5 watt, model number 118399; (416)697-96141]. Likewise a preferred embodiment of the gear head or gearbox 14*b*** is also available front Maxon Precision Motors, Inc. [Ø10 mm, 0.1 Nm max. torque, 1024:1 reduction ratio, model number 110312].

This positive displacement arrangement results in a very precise uniform flow rate of product through the device and thus onto the recipient, thus permitting a substantially uniform application of the product. This can also result in a reduction in the amount of product needed to achieve the desired result. For example, in at least one embodiment, less than 0.5 grams of product can be used per application. Further, the speed selection switch 9 (discussed in more detail below) permits at least two constant flow rates. These flow rates can preferably be from about 0.05 milliliters of product per minute to about 0.5 milliliters of product per minute. Further, in at least one embodiment, the torque transmitted by the motor **14*a* and gearbox 14*b*, to the actuator 11, can be about 5 times the actual torque needed to dispense the product from the cartridge 31. This excess torque thereby essentially ensures a constant steady flow rate throughout each, and during each, application of the product from the cartridge 31** regardless of any changes in tolerances which may occur.

To further explain, as seen in FIG. 3A, the casing 10 provides an internal product chamber or reservoir 38 for containing the product to be sprayed. In at least one embodiment, each disposable cartridge reservoir 38 can contain about 2 or 3 milliliters of product. The movement of the piston 6 pressurizes the reservoir 38, and thus delivers the product to the nozzle 4, which nozzle 4 is disposed on the opposite end of the disposable cartridge 31 from the actuator 11. Since this inventive cartridge 31 is essentially in the form of a novel syringe which is engaged and driven by a direct drive motor, the disclosed positive displacement mechanism can deliver a target flow rate with great accuracy and precision.

As shown in FIG. 3A, the electrode 3 can be disposed adjacent the nozzle 4. In at least one embodiment this electrode 3 can be an injection molded 40% carbon-fiber filled Acrylonitrile Butadiene Styrene(ABS) component. This 40% carbon-fiber filled Acrylonitrile Butadiene Styrene (ABS) is commercially available from RTP Company 580 East Front Street, Winona, Minn. 55987 [RTP 687 Acrylonitrile Butadiene Styrene (ABS) 40% Carbon Fiber PAN reinforced; (800) 433-4787]. In at least one embodiment, the carbon fibers could possibly be disposed substantially length-wise in the direction of flow of the current through the electrode.

The electrode 3 includes, or forms, two plug seals 35, one sealing against the casing 10 and the other sealing against the nozzle 4 (these seals 35 are discussed in more detail below). The electrode 3 can also have an extension leg or legs 36 which can be designed to fit into a corresponding recess or receptacle on the left housing 17 of the spraying device. Extension leg 36 can thereby prevent the disposable cartridge 31 from rotating during operation. Extension leg 36 of the electrode 3 also can make contact with the high voltage contact 2 which can be located on the left housing 17 to permit the electrical charging of the electrode 3 by the high-voltage power supply 1. In at least one embodiment of the invention, extension leg 36 can be in the form of a tab (as shown), in a different embodiment the extension leg 36 can be in the form of an annular rim or contact **36*a* about the exterior of the casing 10 (see FIGS. 17A–17**D).

The electrode 3 and high voltage contact 2 can be made of a variety of materials, for example, conductive plastic or metal, such as copper. In at least one embodiment this high voltage contact 2 can be an injection molded 40% carbon-fiber filled Acrylonitrile Butadiene Styrene(ABS) component. The carbon fiber can be disposed substantially lengthwise, in the direction of current flow in the contact. This 40% carbon-fiber filled Acrylonitrile Butadiene Styrene (ABS) is commercially available from RTP Company 580 East Front rife Street, Winona, Minn. 55987 [RTP 687 Acrylonitrile Butadiene Styrene (ABS) 40% Carbon Fiber PAN reinforced; (800) 433-4787].

The nozzle 4 provides an orifice 39 for the product, to thereby direct the flow of the, product. The electrode 3 is disposed to charge the product that has been moved from the reservoir 38 into the orifice 39. Once the charged product exits orifice 39, droplets are formed by electrostatic repulsion as the charged fluid is dispersed.

Figure 4:
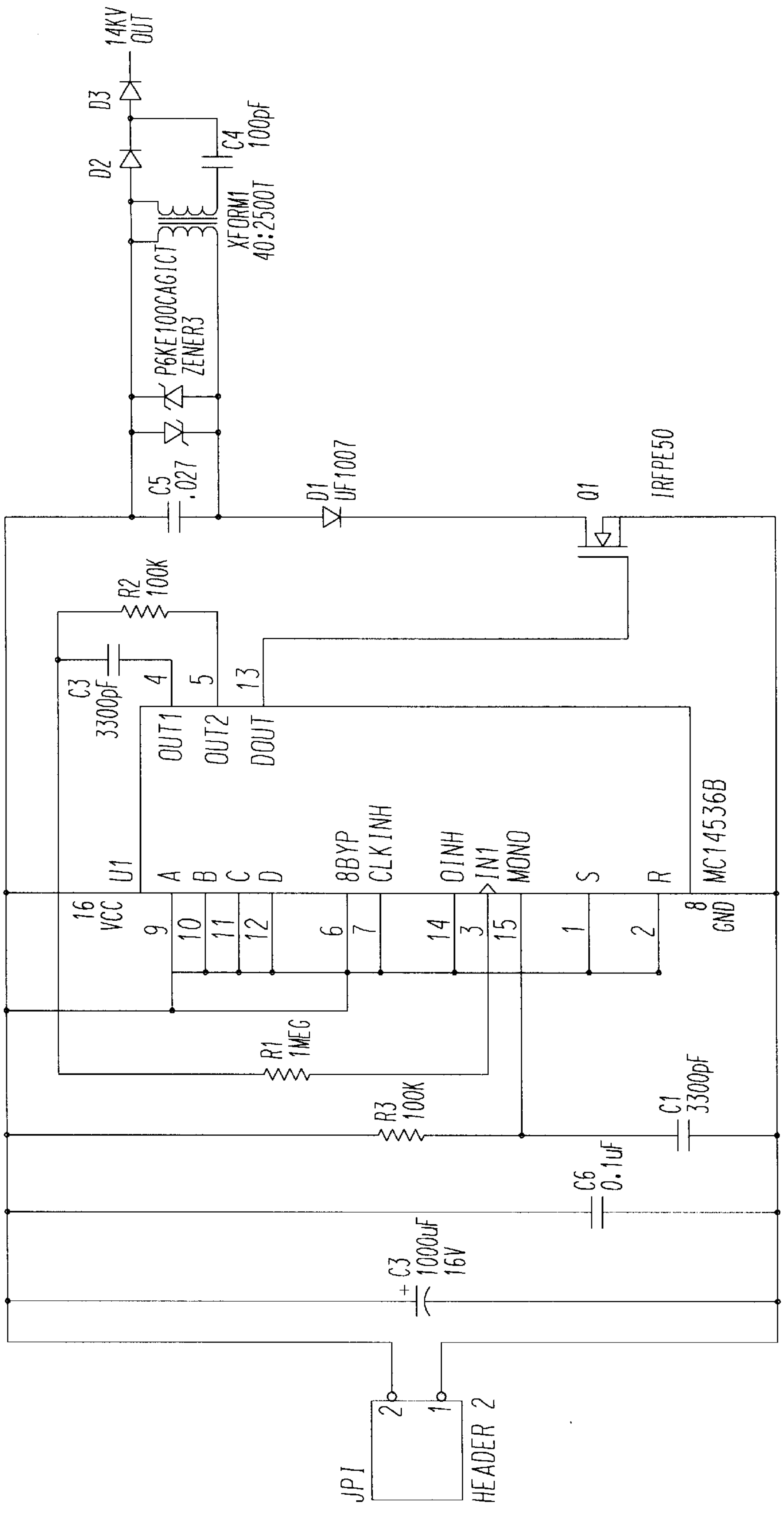
FIG. 4 is a schematic of a possible arrangement for a controller circuit of the high-voltage power supply.

FIG. 4 shows a schematic of one possible embodiment of the controller circuit 18 (see FIG. 1) for the high voltage power supply 1 used to charge the electrode 3. The high voltage power supply 1 can include a transformer, a high voltage assembly and the controller circuit 18. This controller circuit 18 can be configured to be essentially separate from the rest of the power supply 1. This controller 18 can generate AC pulses which can be controlled to be about 200 volts, peak to peak. This signal can then be stepped up to about 8,000 volts by the transformer and can then be nearly doubled in the high voltage assembly. The circuit topology can be that of a flyback transformer. This type of circuit can be used to generate low cost high voltage power supplies, wherein the underlying principle is to use the inductive spike that results when the current direction is switched in an inductor to generate a high voltage pulse.

The second portion of the circuit 18 can include the flyback transformer and a high voltage rectifier/doubler. The transformer can increase the approximate 200 volt input to approximately 8,000 volts. The transformer can have, for example, 40 turns on the primary coil and 2,500 turns on the secondary coil. The high voltage structure can have diodes D2 and D3 and capacitor C4 can be configured as a charge pump that nearly doubles the AC input voltage, resulting in a output of about 14KV.

In at least one embodiment, to minimize electrical leakage and corona, the transformer and the high voltage structure can be encapsulated in epoxy. Further, in at least one embodiment a potentiometer can be used in place of resistor R3 to permit the final voltage output to be adjusted, and permit compensation for sub-nominal batteries. An additional resistor can also be added to limit the current output, for example, a 1 gigaohm (1 billion ohms) resistor can be used to limit the current output to approximately 10 microamp.

Figure 5:
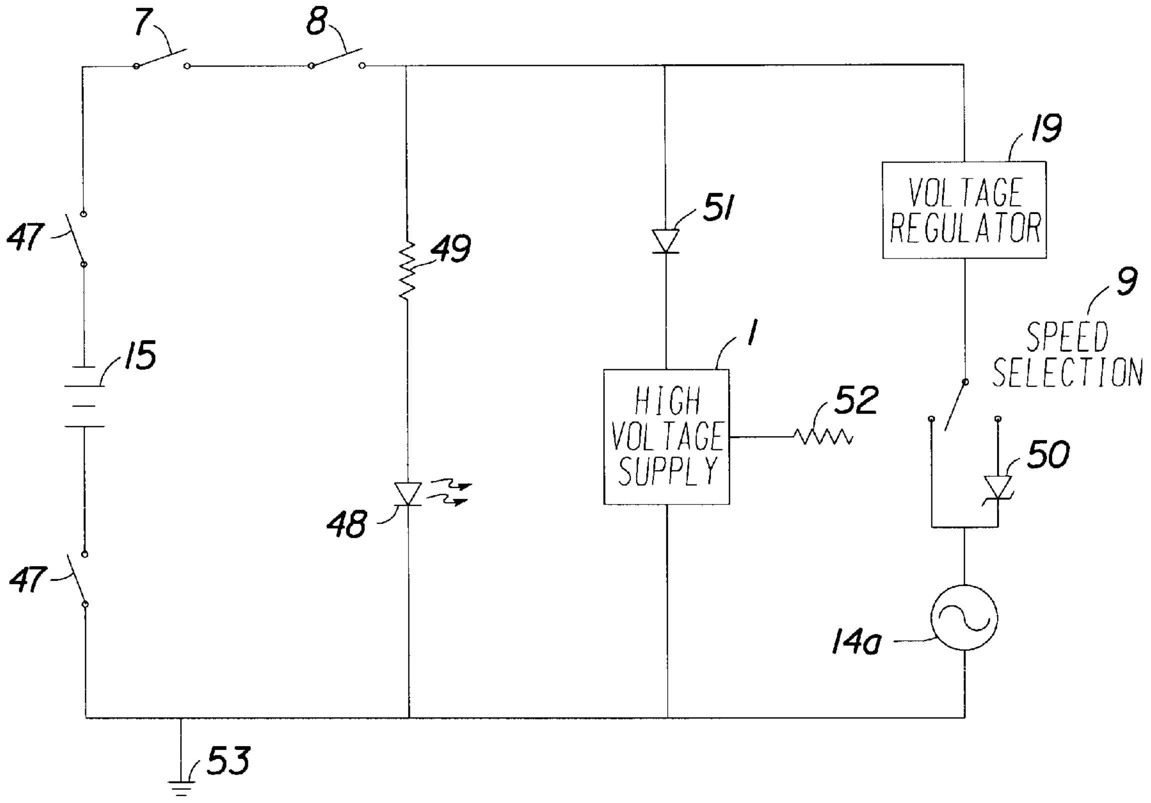
FIG. 5 is a schematic of a possible arrangement for the spraying device circuit.
Figure 9:
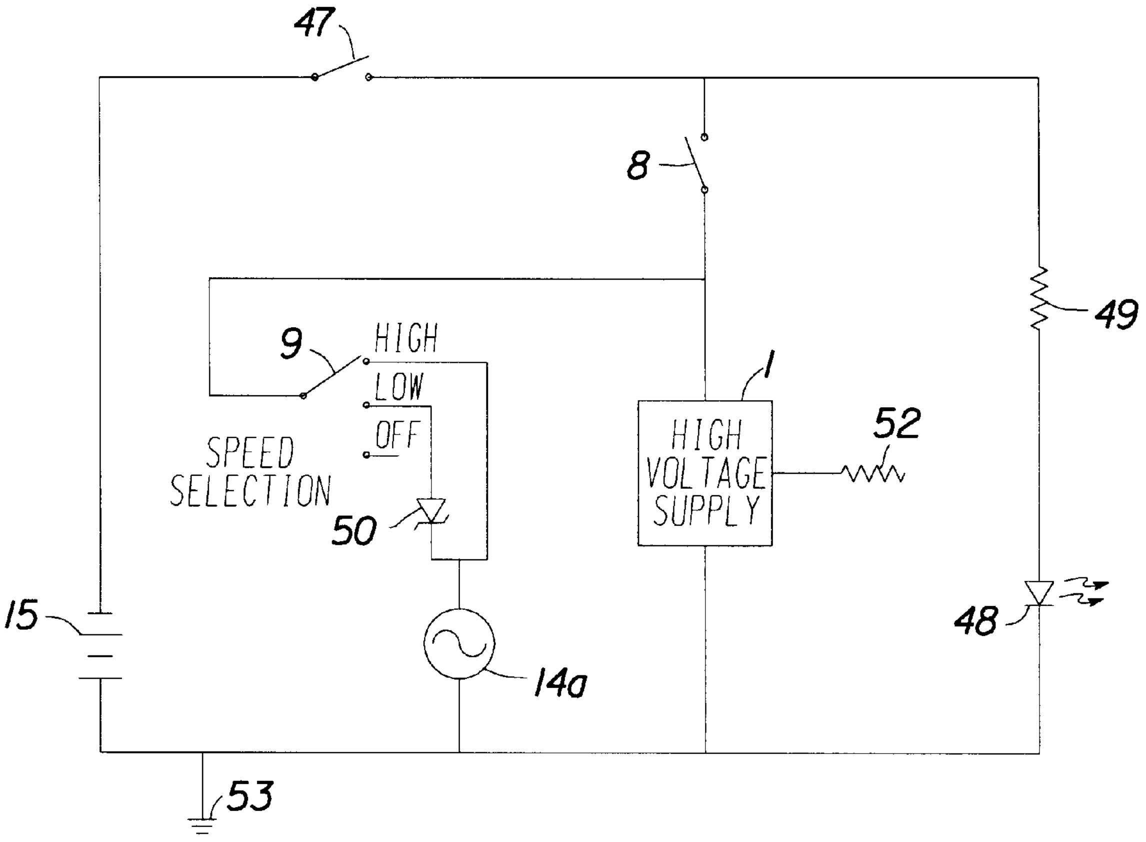
FIG. 9 is a schematic of another possible arrangement for the spraying device circuitry.

FIGS. 5 and 9 illustrate circuit diagrams of different arrangements for circuitry which may be used with at least one embodiment of the inventive electrostatic spraying device. The power supply 15 shown is a battery. In at least one preferred embodiment this power supply can be a user replaceable battery or batteries, for example, a standard "9V" battery. It is also within the scope of the present invention that this power supply could vary, for example, the power supply could be user-rechargeable cells, a non-user serviceable rechargeable power pack, or an external source (i.e. "line" supply).

In at least one embodiment the power supply 15 can be separated from the rest of the circuit by an "ON" switch 47. This switch 47 can provide the benefit of prolonging the active life of a self-confined power supply 15 such as a battery, as well as potentially adding a margin of safety to a line-voltage power supply, wherein only when the "ON" Switch 47 is closed is voltage then supplied to the remainder of the circuit. One preferred embodiment for the switch 47 would be a toggle design, which would maintain its setting until its next actuation.

As explained above, a safety switch 7 can be included (see FIGS. 5 and 2A) which is actuated when the cap 5 is placed on the housing. This switch 7 is designed to prevent the accidental shocking of a user of the device by coming in contact with the high voltage contact 2. This switch preferably is of the "momentary" type such that it maintains a normally open position when it is not activated, and forms a closed circuit upon activation.

In FIG. 5, the "on-off" or apply switch 8, which is depressed or turned to the "on" position by the user, depending on the type of switch employed, completes the power supply circuit, sending power to the drive motor **14*a* branch, the high voltage power supply 1 branch and the power on indicator 48 branch. Each branch can be in parallel to one another. The power-on indicator 48 can be an LED that emits light in the green range of the visible EM (electromagnetic) spectrum. As shown in FIG. 5, this indicator 48 can serve to indicate both that the product is being both charged by the electrode 3 and/or dispensed by the motor 14*a***.

In FIG. 9 the circuitry arrangement is different, wherein the indicator 48 indicates when the "ON" switch 47 is actuated, thereby indicating that power is available to be sent to the other branches once the apply switch 8 is activated, and the circuit is completed. Since the shown power-on indicator 48 is an LED an impedance 49, with a preferred current value of about 560 ohms, serves as a current-limiting device. This impedance 49 may be a separate component or may be integrated into an LED lamp assembly, or may be eliminated if a different type of power-on indicator 48 is used which does not require it.

The speed selector switch 9, allows the user to choose between a "high" speed and a "low" speed for the dispensing of the product by the motor **14*a***. The high speed, for example, could provide a motor speed of about 6.6 RPM, and a product flow rate of about 0.5 ml/min. The low speed, for example, could provide a motor speed of about 1.1 RPM, and a product flow rate of about 0.05 ml/min.

A voltage regulator 19 controls the input voltage to the motor **14*a*. The nominal voltage output from the voltage regulator can preferably be about 3.3 volts. To achieve the high speed, the speed selector switch 9 sends this full voltage directly to the motor. To achieve the low speed the speed selector switch sends this voltage through a voltage reducing device 50, for example, a Zener diode, which reduces the voltage supplied to the motor to preferably about 2.6 volts. This speed selector switch 9** could have a variety of forms, for example, it could be a toggle-type switch.

In the arrangement shown in FIG. 5, to permit the current to flow in only on, direction a rectifier diode 51 is included. This rectifier diode 51 can prevent damage to the high voltage power supply from voltage being applied in the wrong direction and additionally prevent the high voltage power supply 1 from sending current to the drive motor **14*a* in the wrong direction. This can occur when the high voltage supply 1 has a capacitor that stores charge and then releases it back through the circuit, which can cause the drive motor 14 to turn in the reverse direction. A rectifier diode 51** is not needed if the possibility of these types of adverse situations are eliminated in other ways.

The current output from the high voltage power supply 1 can be limited by a variety of mechanisms. For example, it can limit its own output or, as shown in FIGS. 5 and 9, a resistor 52 can be placed in series with the power supply 1 output. The resistor 52 can preferably have a value of 1,000,000,000 ohms (1 gigaohm).

To help avoid electrostatic shock to the user and to aid in the dispersal of the product, a ground contact 53 can establish a ground between the device circuits and the user. This ground can prevent the building-up of potential between the user and the device, which can result in an electrostatic shock to the device user. Further this ground can prevent charge from building-up on the skin of the user as the charged particles accumulate on the face of user, which charged particles on the skin could possibly repel additional product that is being applied to the same area. Therefore, when the user of the device is not the recipient of the product, such as in a salon setting, it can be advantageous for the recipient to remain in constant or occasional contact with the user of the device. Preferably, this ground contact 53 is integrated into, and/or is substantially adjacent to, the apply switch 8, wherein the user cannot energize the high-voltage power supply without simultaneously grounding herself to the device. The apply switch 8 can be made of metal and/or a conductive contact or a grounding electrode can be located next to the apply switch 8, for example.

Figure 6:
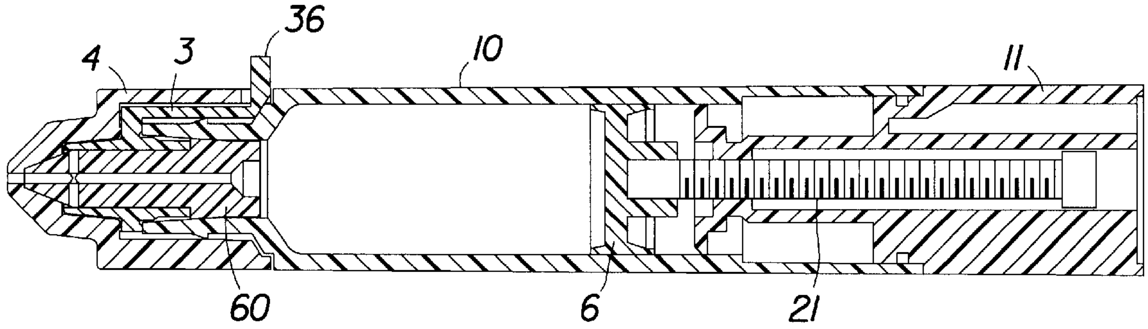
FIG. 6 shows a cross-sectional view of one embodiment of the cartridge.

FIG. 6 shows one embodiment of the inventive disposable cartridge 31. These cartridges 31 are designed to contain multiple applications of product, and to be easily removed from the device, and disposed by the user, once the cartridge product supply is substantially depleted or is no longer desired. A new cartridge 31, containing the same or different product, can then be easily inserted by the user into the device. Further, this type of inventive disposable cartridge 31 can have the additional benefit of having the spray nozzle 4 as a component of the cartridge 31 itself, rather than as part of the spraying device. This provides the user with a new clean, unclogged nozzle 4 each time a new cartridge 31 is installed into the device, thereby requiring less maintenance of the device, on the part of the user. However, it is also within the scope of at least one embodiment of the present invention that these cartridges 31 could potentially be designed such that the nozzle might be separate from, or part of, the device rather than part of the cartridge 31. Likewise, the electrode 3 could also be designed to be part of, or separate from, the device, rather than part of the cartridge 31. Further, it is also possible that the cartridges 31 could be designed to be refillable, rather than disposable.

Figure 7:
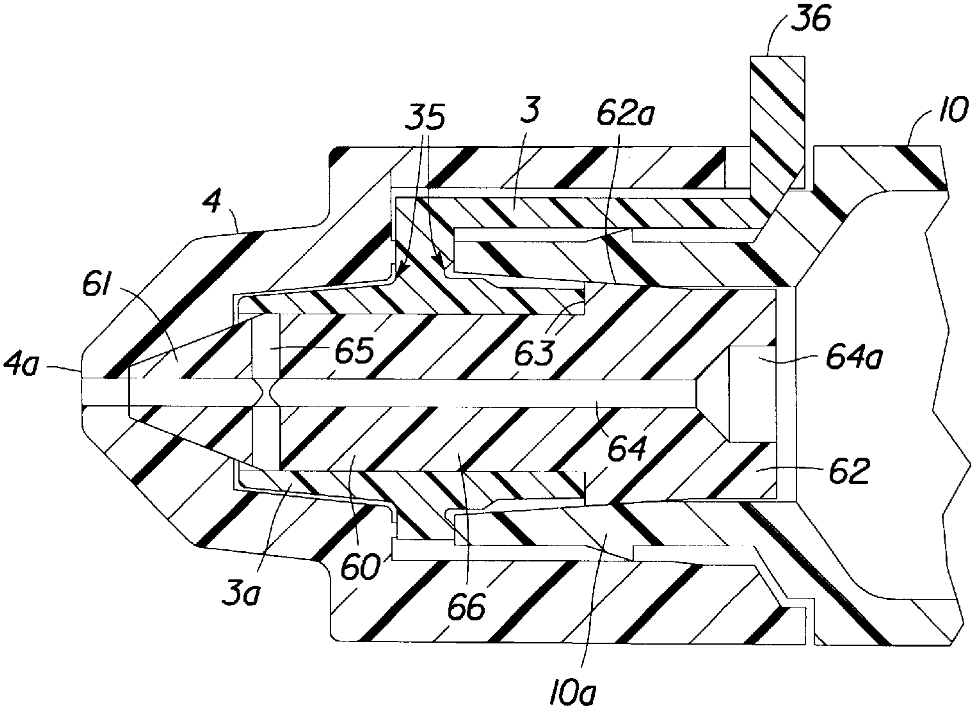
FIG. 7 shows a cross-sectional view of the nozzle-end of one embodiment of the cartridge.

As shown in FIG. 6 and FIG. 7, in at least one embodiment, an insulator 60 can be disposed within the nozzle 4. The nozzle 4 can have a tip 4*a* (see FIG. 7). The insulator 60 can be substantially cylindrical in shape, with one end, disposed closest to the nozzle tip, having a conical tip portion 61. The opposite end of this insulator can have a substantially cylindrical portion 62, and a narrower substantially cylindrical portion 66 can be located between the two end portions, such that an annular shaped ledge 63 is formed between the two substantially cylindrical portions 62, 66. On this ledge 63 the electrode 3, having a substantially annular body portion 3*a* can be positioned around the exterior surface of the insulator 60, with the electrode extension leg 36 extending therefrom. As shown in FIG. 7, the wider end 62 of the insulator 60, which wider end 62 slightly tapers, and a portion of the electrode body 3 a can be inserted onto a collar portion 10*a* of the casing 10 of the disposable cartridge 31. The exterior surface of the wider end 62 can serve as a plug, forming a plug seal 62*a* with the collar portion 10*a*. An annular rim on the electrode 3 as well as two substantially annular portions extending from this rim, serve as two plug seals 35, with one side forming a plug seal 35 sealing against a portion of the casing collar portion 10*a*, and the opposite side forming a second plug seal 35 sealing against a portion of the nozzle 4.

A very narrow product flow pathway or channel 64 runs through the center of the insulator 60. Channel 64 has a wider-channel-portion 64*a* on the end closest to reservoir 38. This wider-channel-portion 64*a* has a "neckdown" section 64*b* connecting it to channel. 64, thereby preferably creating product turbulence at this point, as the product passes from the wider-channel-portion 64*a* to channel 64. The channel 64 serves to further restrict the flow of the product. Another channel or aperture 65 is disposed through the insulator 60, substantially transverse to channel 64. Aperture 65 serves to focus the charge from the electrode 3 through aperture 65 to the product as it moves past aperture 65, prior to the product being dispersed from the nozzle 4, thereby electrostatically charging the product. Aperture 65 is positioned within the insulator 60 at a distance substantially closer to the tip 4*a* of the nozzle 4, than to the product supply in reservoir 38. In this manner, namely, by restricting the product flow through channel 64, and positioning aperture 65 closer to the nozzle tip 4*a*, the electrical charge from the electrode 3 that travels back to the product supply in reservoir 38 can be minimized.

In at least one embodiment the insulator 60 and the nozzle 4 can be made from Delrin, which is commercially available from E.I. du Pont de Nemours and Company (Dupont), 1007 Market Street, Wilmington, Del. 19898 [Delrin 500P (NC010, Medium Viscosity Acetal); (800) 441-7515]. The piston 6 can be made from a variety of materials, such as, high-density polyethylene(HDPE), commercially available from Dow Chemical Company, Midland, Mich. [High Density Polyethylene (HDPE), 30460M, Fluorine treated; 800-232-2436]; or from low-density polyethylene (LDPE), fluorine treated. The actuator 11, for example, can be formed from acrylonitrile butadiene styrene (ABS), or from 20% Calcium Filled Polypropylene (PP), which is commercially available from Ferro Corporation, 1000 Lakeside Avenue, Cleveland, Ohio 44114 [20% Calcium Filled Polypropylene (PP), High Gloss, GPP20YJ3395DK; (216) 641-8580)]. Casing 10 can be formed from Barex 210, which is commercially available from BP Chemicals, Inc., 440 Warrensville Center Road, Cleveland, Ohio 44120 [Barex 210 Injection Grade, impact modified acrylonitrile-methyl acrylate copolymer; (216) 586-5847]. The housing 17, 20 and cap 5, can preferably be formed from Magnum 545 Acrylonitrile Butadiene Styrene (ABS), this can be purchased from Dow Chemical Company, Midland, Mich. [800-232-2436].

In one embodiment the nozzle, electrode and insulator can be formed as one integral part, formed for example by two shot molding. Preferably, the first plastic material molded can be white Delrin, and the second plastic material can preferably be the conductive ABS. Known multi-shot injection molding techniques provide the advantages of permitting multiple colors and/or materials to be sequentially injected in a single, continuous process, and thereby speed throughput, and minimize production and assembly operations. Multi-shot injection techniques can also result in a variety of benefits and cost savings, such as in machinery, labor and utilities, for example.

In one embodiment of the disposable cartridge 31, there can be a distance of about 0.5 inches between the product supply and the center of aperture 65, and about 0.25 inches from the center of aperture 65 to the very tip 4*a* of nozzle 4, thereby forming about a 2:1 distance ratio. A distance of about 0.170 inches can be between the center of aperture 65 and the extreme tip of the conical portion 61 of the insulator 60.

Figure 8:
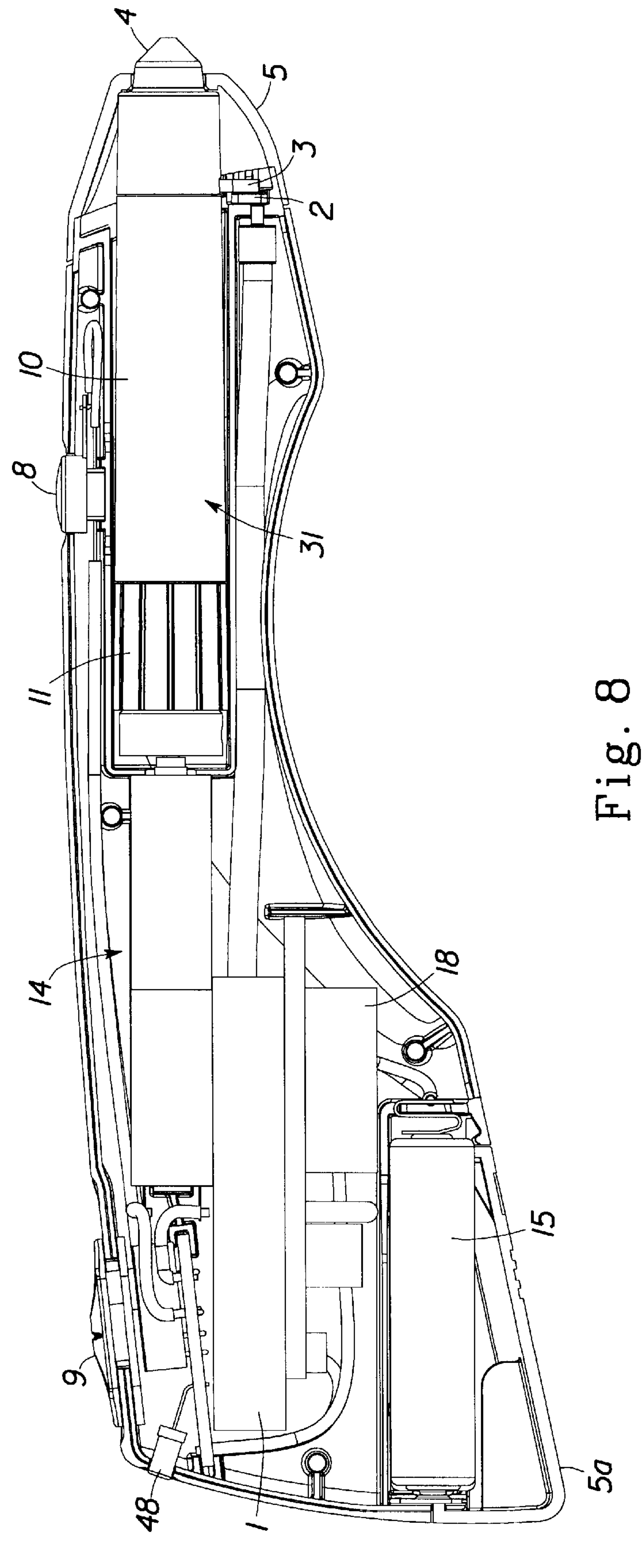
FIG. 8 shows a cross-sectional view of another embodiment of the electrostatic spraying device.

FIG. 8 shows a cross-section of another embodiment of the electrostatic spraying device, wherein the same or similar components have been given the same reference numbers as the embodiment shown in FIG. 1.

Figure 10:
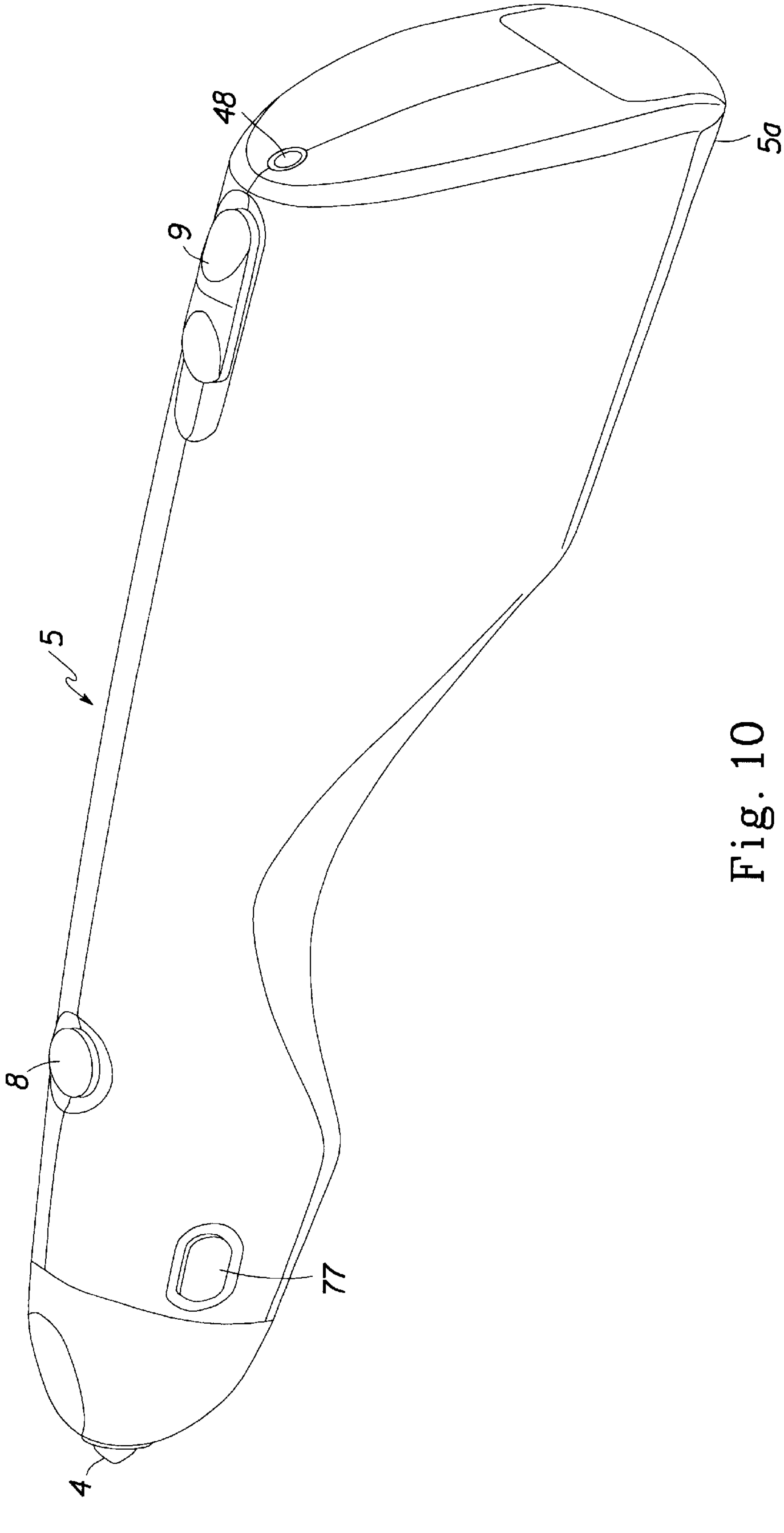
FIG. 10 shows a perspective view of the exterior of the embodiment shown in FIG. 8.

FIG. 10 shows a perspective view of the exterior of the embodiment of this electrostatic spraying device shown in FIG. 8. This housing has a sleeker design than the previously discussed embodiment. This embodiment has an additional housing component 5*a*, which is a removable cover allowing easy access to the battery, or batteries 15. The cap 5, for the insertion of the cartridge, in this embodiment attaches to the front portion of the housing, and has a release button 77 to aid in its removal. Additionally, a separate power-on indicator 48 is positioned on the back of the device. The speed selector switch 9 can have 3 positions, for example, a high, low and power off position.

Figure 11:
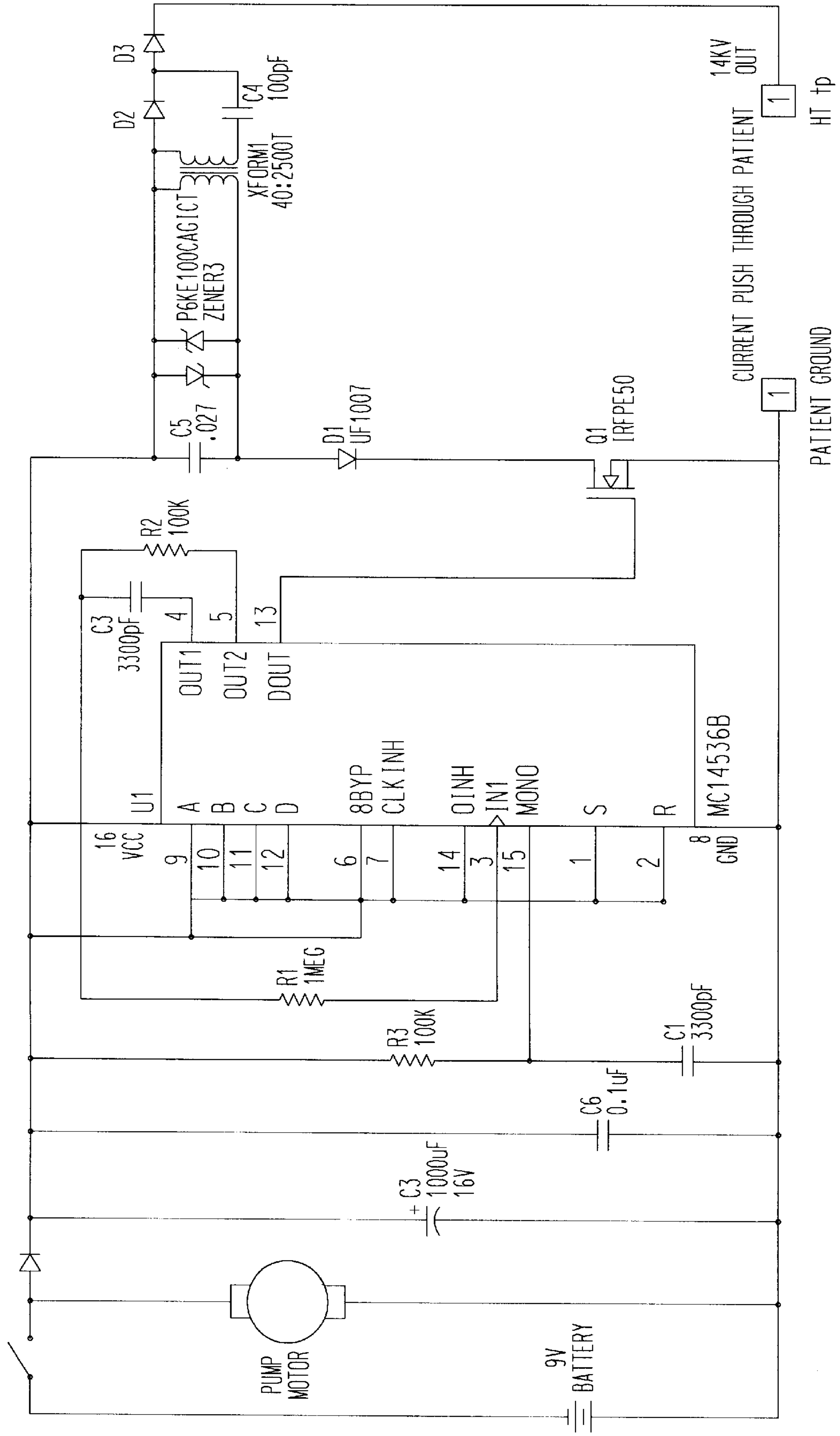
FIG. 11 shows a schematic for a possible circuit arrangement for at least one embodiment of the electrostatic spraying device.

FIG. 11 shows a schematic for another possible circuit arrangement for at least one embodiment of the electrostatic spraying device, including circuitry for the motor power supply and the high voltage power supply.

FIG. 12A shows a top view of one possible embodiment of the insulator 60. FIGS. 12B and 12C show cross-sectional views of the embodiment shown in FIG. 12A. Channel 64 has a diameter of about 0.03 inches in this embodiment. Channel 64 can preferably have a diameter of about 0.020 to 0.030 inches. A groove or pathway 78 can also be formed at the tip of the insulator 60 to thereby focus the charge from the electrode 3 through this groove 78 and to the product prior to its dispersal to nozzle tip 4*a*. Additionally, in this embodiment the wider-channel-portion 64*a* encompasses a substantially larger portion of the wider substantially cylindrical end 62 of the actuator 60. FIG. 12D shows a perspective view of this same embodiment.

Figure 13A:
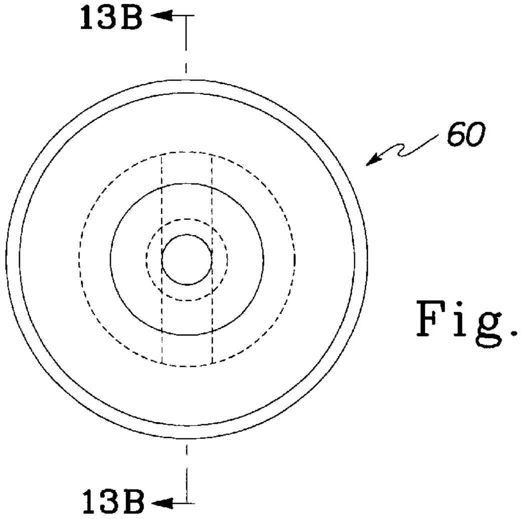
FIGS. 13A shows a top view of another embodiment of the insulator.
Figure 13B:
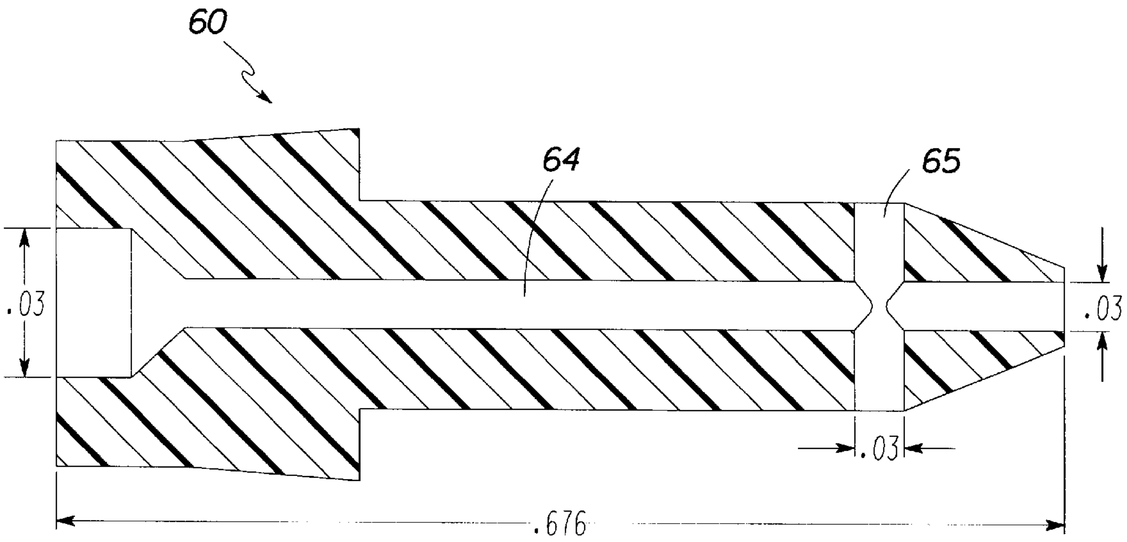
FIG. 13B shows a cross-sectional view of the insulator embodiment shown in FIG. 13A.

FIGS. 13A shows a top view and FIG. 13B shows a cross-sectional view of another possible embodiment of the insulator 60. In this embodiment the insulator 60 contains the aperture 65 which, as discussed above, serves to focus the charge from the electrode 3 to the product as it passes aperture 65. Aperture 65 can preferably be about 0.020 to 0.030 inches in diameter.

Figure 14A:
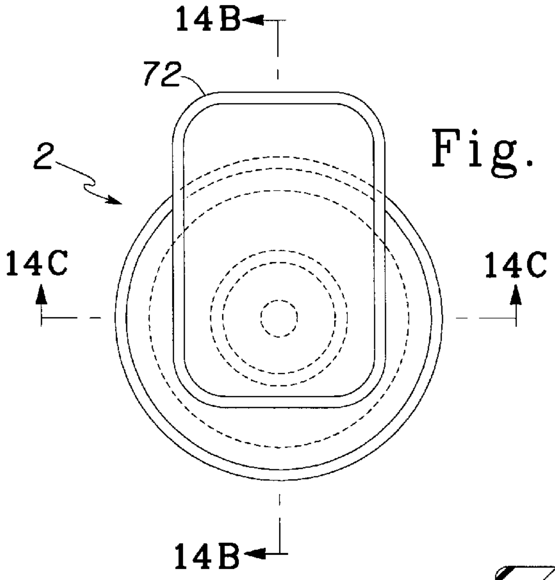
FIG. 14A shows a top view of one embodiment of the high-voltage contact.
Figure 14B:
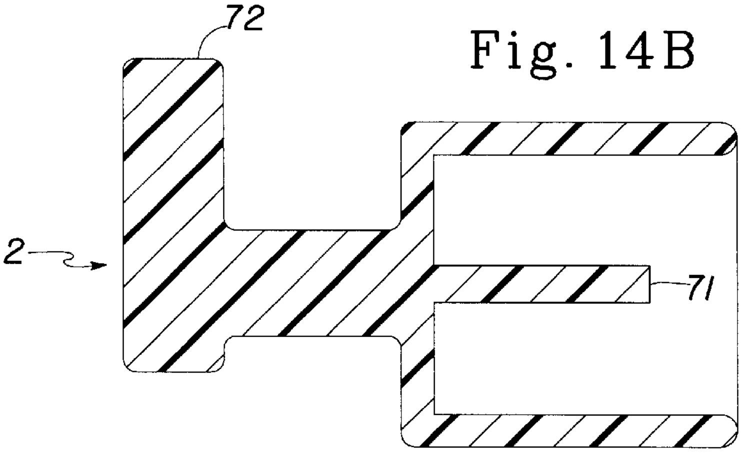
FIGS. 14B and 14C show cross-sectional views of the same embodiment of the high-voltage contact as shown in FIG. 14A.
Figure 14C:
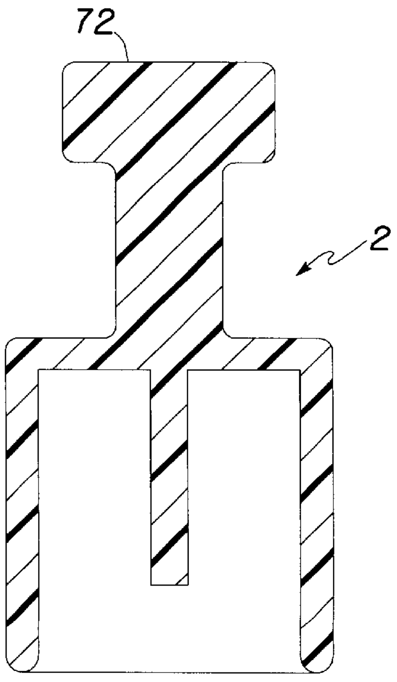
Figure 14D:
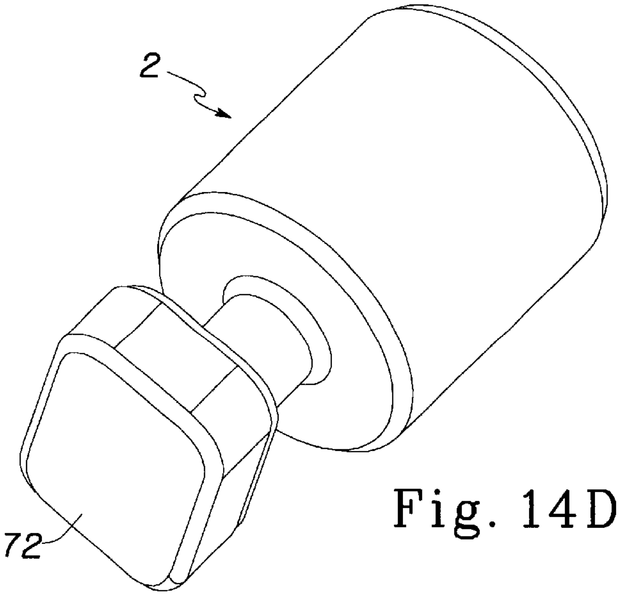
FIG. 14D shows a perspective view of the high-voltage contact shown in FIG. 14A.

FIG. 14A shows a top view of one possible embodiment of the high-voltage contact 2, which contact 2 provides charge to the electrode 3, as discussed above. An end contact portion 72 makes electrical contact with the electrode 3 and electrical connection 71 connects the contact 2 to the high voltage power supply 1. This electrical connection 71 can be in the form of a spade connection, for example. FIGS. 14B and 14C show cross-sectional views of this same embodiment and FIG. 14D shows a perspective view of this embodiment of the contact 2.

Figure 15:
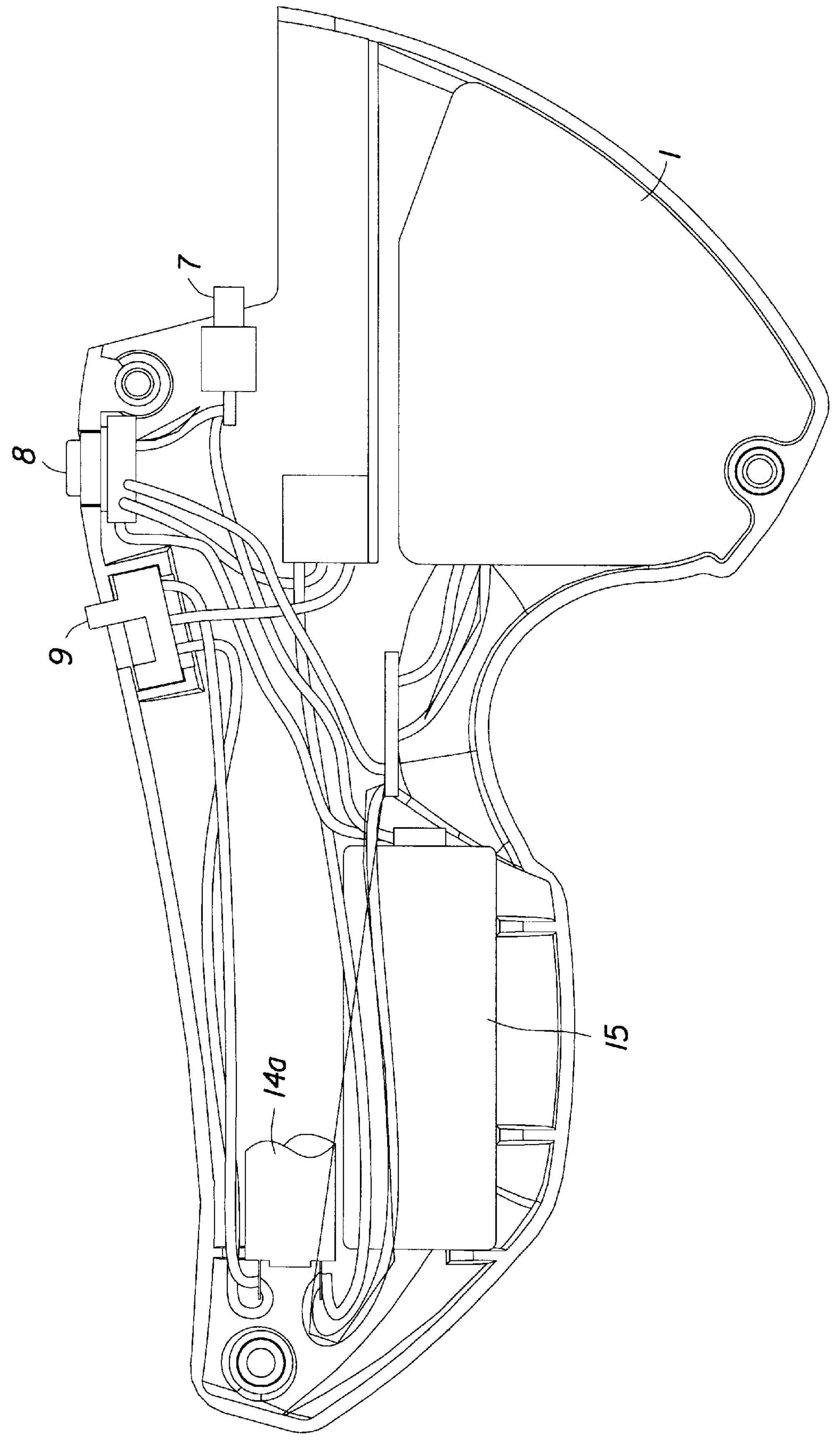
FIG. 15 shows a schematic of a wiring diagram for one embodiment of the electrostatic spraying device.

FIG. 15 shows a schematic of a wiring diagram for one embodiment of the electrostatic spraying device.

Figure 16B:
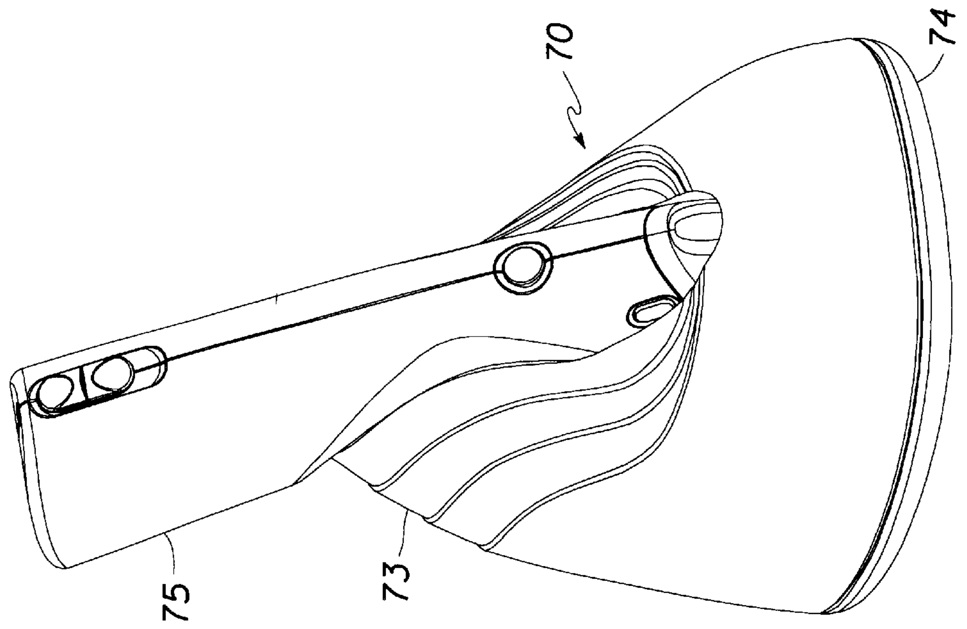
FIG. 16B shows a perspective view of the same stand and device shown in FIG. 16A.
Figure 16A:
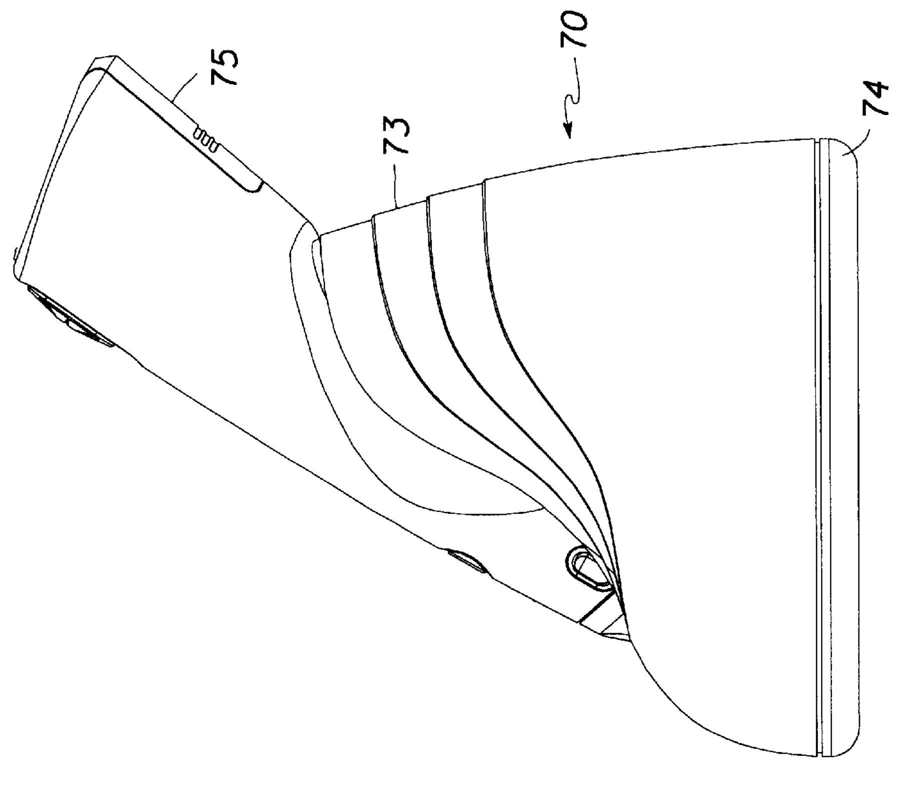
FIG. 16A shows a side view of a possible embodiment of a stand for the electrostatic spraying device with the device therein.

As shown in FIGS. 16A and 16B, a stand 70 can also be provided. This stand 70 can be preferably made from plastic, and is designed to permit the nozzle end of the device to be inserted past a receiving or neck portion 73 with metal insert (not shown) of the stand 70, and into a base portion 74. This base portion 74 can be designed to rest upon a surface. The neck portion 73 can be configured to provide support to a bottom edge or surface 75 of the device. Not only can this stand provide a convenient resting or storage spot for the device, it will also allow any residual charge which may have built-up on the device and/or the product therein to dissipate out through the stand.

Figure 17A:
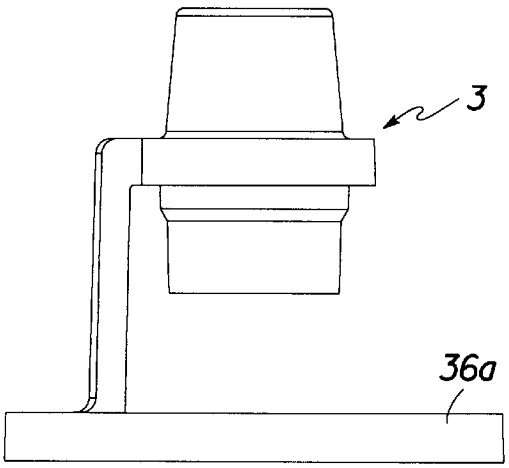
FIG. 17A shows a side view of another embodiment of the electrode having an annular contact.
Figure 17B:
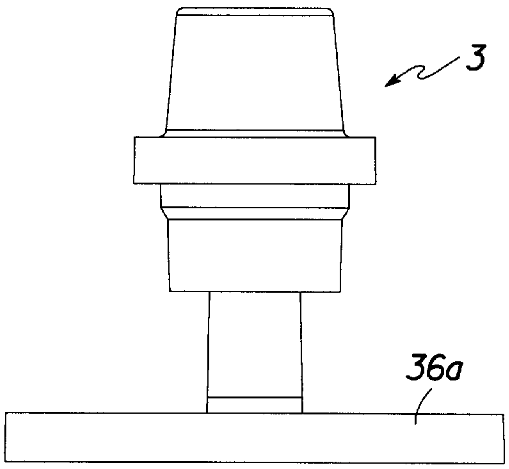
FIG. 17B shows a front view of the electrode shown in FIG. 17A.
Figure 17C:
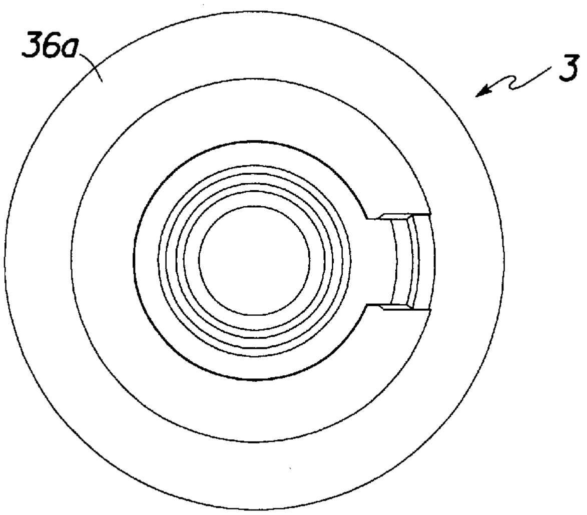
FIG. 17C shows a top view of the electrode shown in 17A.
Figure 17D:
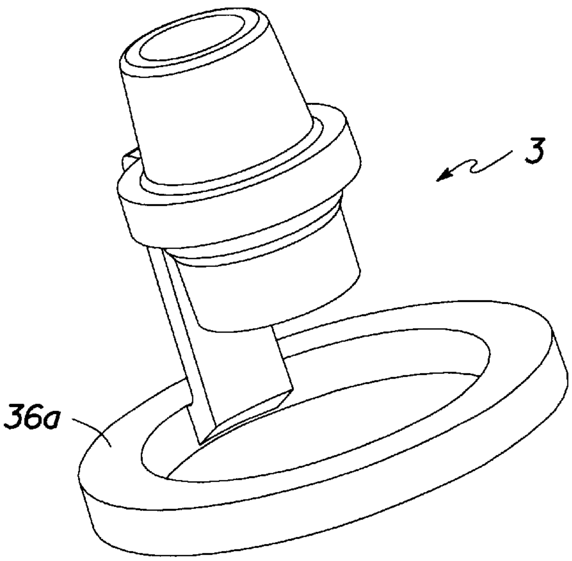
FIG. 17D shows a perspective view of the electrode shown in FIG. 17A.

FIG. 17A shows a side view of another possible embodiment of the electrode 3. In this embodiment of the electrode, the contact or extension leg can be in the form of an annular rim or protrusion 36*a*. This annular contact 36*a* can be configured to encircle the exterior surface of casing 10. The remainder of this electrode 3 can be designed substantially the same or similar to the previously described electrode embodiment which has the contact in the form of an extension leg 36. FIGS. 17B–17D show additional views of this embodiment of the electrode 3, wherein FIG. 17B shows a front view of the electrode 3, FIG. 17C shows a top view of the electrode 3 and FIG. 17D shows a perspective view of the electrode 3.

Figure 18A:
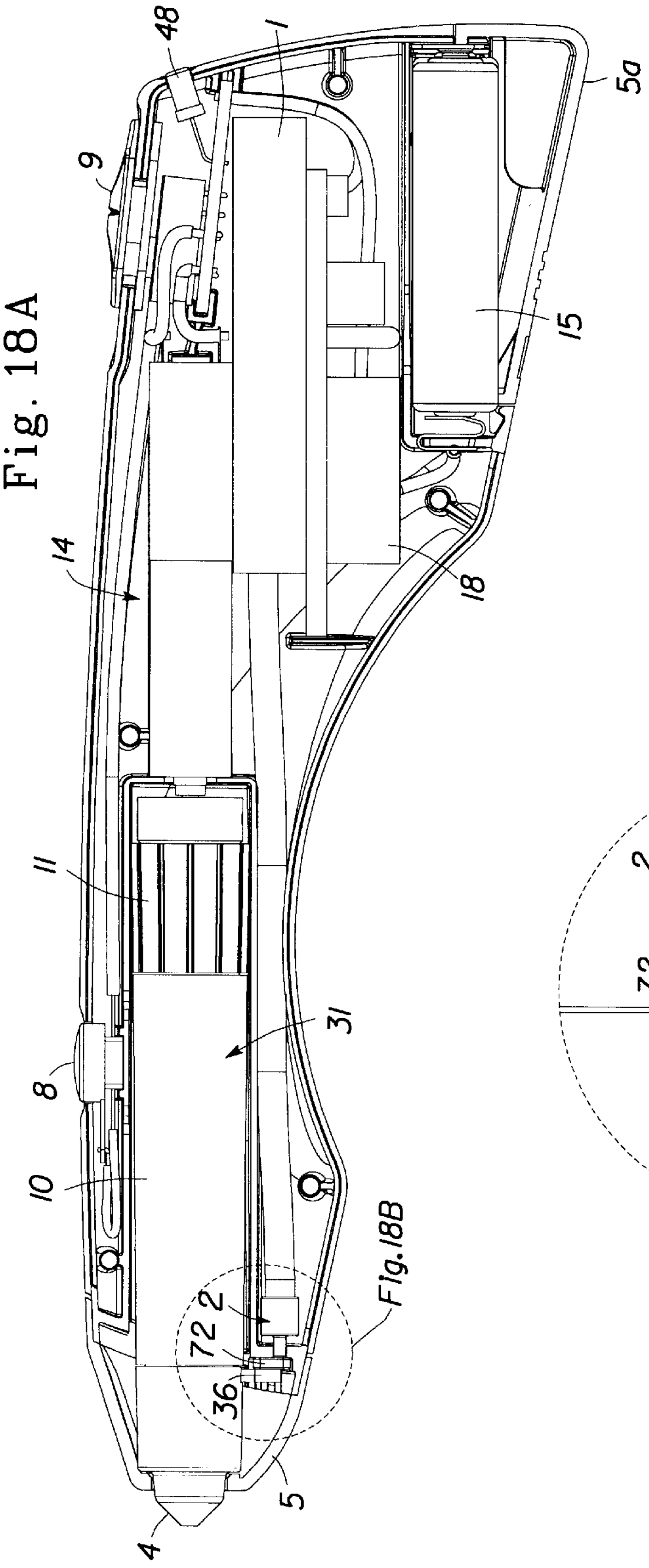
FIGS. 18A and 18B show essentially the same embodiment of the present invention as shown in FIG. 8, with FIG. 18B showing an enlarged view of a contact area.
Figure 18B:
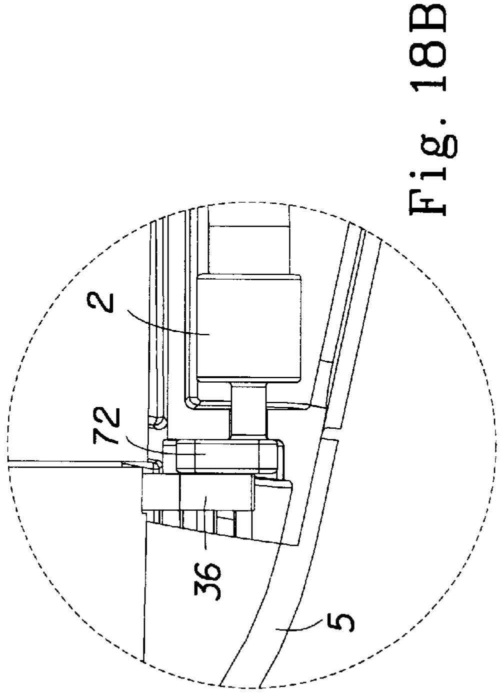

FIGS. 18A and 18B show essentially the same embodiment of the present invention as shown in FIG. 8, with FIG. 18B showing an enlarged view of the contact area between the end contact portion 72 of the high voltage contact 2, and the extension leg 36 of the electrode 3.

Figure 19A:
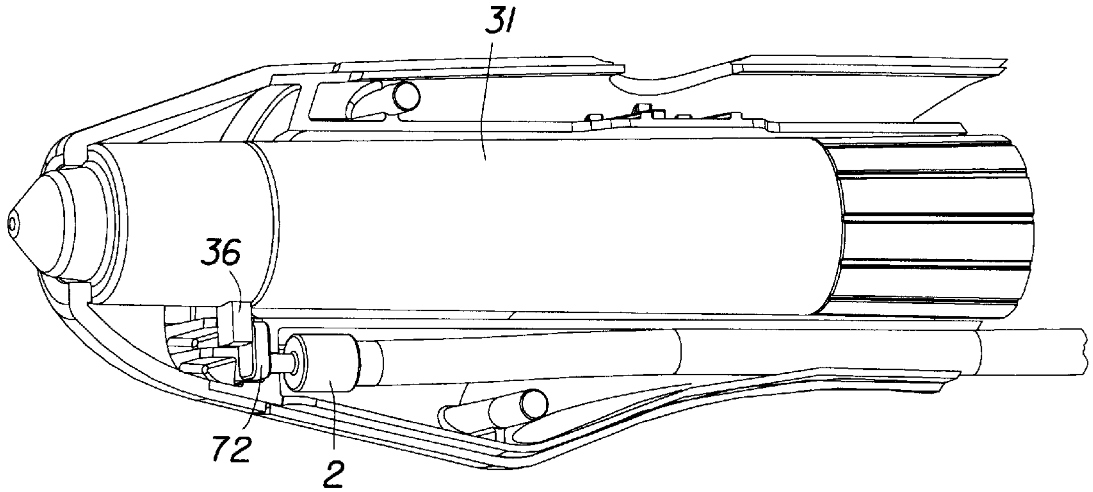
FIG. 19A shows another perspective view of the same or similar contact area as shown in FIG. 18B.
Figure 19B:
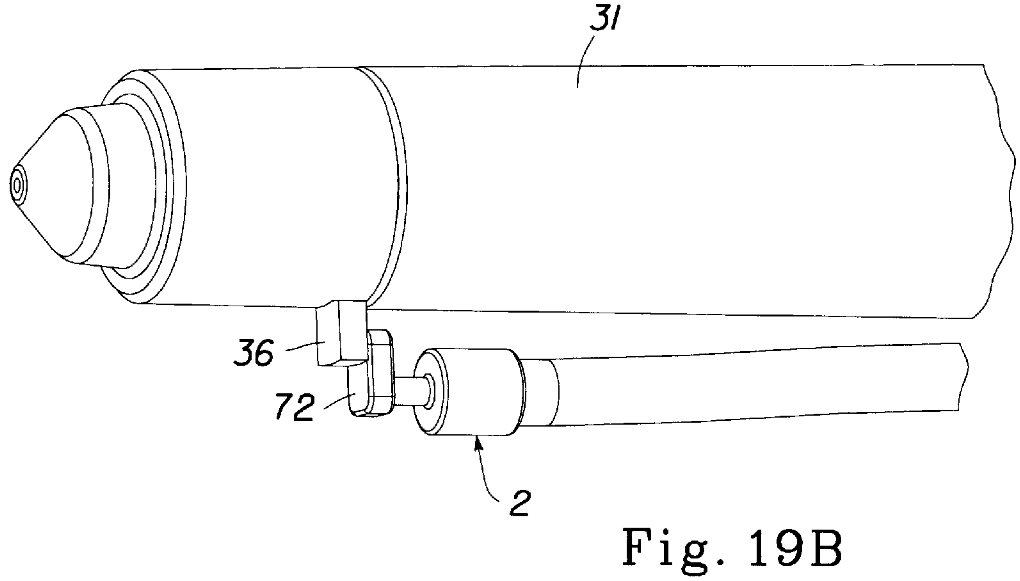
FIG. 19B shows a simplified view of the same area shown in FIG. 19A.

Likewise, FIG. 19A shows another perspective view of the contact area between the electrode 3 and the high voltage contact 2. FIG. 19B shows a simplified view of this same area, showing the cartridge 31 with the extension leg 36 extending therefrom and in contact with the contact portion 72 of the high voltage contact 2.

The inventive device can be used to spray on a variety of products, including numerous personal care products, such as make-up, perfume, medical products, deodorants, etc. In particular, the inventive device is well-suited for the application of a topical product, especially a cosmetic foundation product to the skin of a recipient.

A preferred cosmetic product is a liquid foundation, and more preferably a multiphase (emulsion) composition that can be sprayed onto the recipient's skin with the electrostatic spraying device disclosed herein. This electrostatic spraying can provide the advantages of low product usage and small particle atomization, allowing the creation of an on-surface deposition of discrete dots of the foundation. That is to say, by electrostatically charging the product, tiny droplets of foundation each having essentially the same charge are formed. Because these droplets have like charges they repel one another and therefore disperse and preferably spray onto the skin as discrete dots, preferably of less than about 150 microns, more preferably less than about 100 microns, most preferably less than about 80 microns (e.g., less than about 30 microns) in average size. Because these dots are preferably non-continuous when deposited on the skin, these dots can camouflage skin imperfections and still allow natural skin tones to be revealed. Further, because the foundation product can be a multiphase formula foundation, one of the phases can possibly comprise a formula which can also permit the recipient's natural skin tones to show in the areas where that phase of the product is deposited on the skin. At the same time, due to the dispersal of the product in the form of non-continuous dots, less product is consumed as compared to conventional techniques, such as a non-charged spray, or manually applied product, which might coalesce into a film or be applied as a film, over the skin.

Preferred multiphase, electrostatically sprayable topical compositions are described in commonly-assigned, concurrently-filed U.S. patent application Ser. Nos. 60/149,566, entitled "Electrostatically Sprayable Topical Compositions Having Insulating External Phase and Conductive Internal Phase", Ser. No. 60/149,586 entitled "Discontinuous Films From Skin Care Compositions", Ser. No. 60/149,585 entitled "Wear Resistant Topical Compositions Having Improved Feel", all of which were filed on Aug. 18, 1999 in the names of Thomas E Rabe, et al. Other preferred electrostatically sprayable topical compositions are described commonly-assigned, concurrently filed U.S. patent application Ser. No. 60/149,565, entitled "Stable, Electrostatically Sprayable Topical Compositions", filed Aug. 18, 1999 in the names of Thomas E Rabe, et al. as well as in the aforementioned Ser. No. 60/149,586 and Ser. No. 60/149,585 applications. The disclosures of each of these applications are hereby incorporated herein by reference.

Other suitable methods, examples, and related details for electrostatically spraying a product are described in the following U.S. patents, all of which are incorporated herein by reference:

U.S. Pat. No. 4,549,243 issued Oct. 22, 1985, entitled Electrostatic Spray Apparatus with Capillary Feed of Liquid to the Spray Nozzle.

U.S. Pat. No. 4,561,037 issued Dec. 24, 1985, entitled Electrostatiic Spraying.

U.S. Pat. No. 4,663,639 issued Dec. 5, 1987, entitled Printer.

U.S. Pat. No. 5,121,884 issued Dec. 16, 1999, entitled Electrostatic Spraying Device, Intended for use in Dispersing Materials Normally Dispersed by Aerosol Sprays.

U.S. Pat. No. 5,932,011, issued Aug. 3, 1999, entitled Electrostatic Spraying Devices with Hazardous Condition Warning System.

All of the patents, patent applications and publications recited herein are hereby incorporated by reference as if set forth in their entirety herein.

The invention as described hereinabove in the context of the preferred embodiments is not to be taken as limited to all of the provided details thereof, since modifications and variations thereof may be made without departing from the spirit and scope of the invention.

What is claimed:

1. A disposable cartridge for use in an electrostatic spraying device, said disposable cartridge comprising:

a reservoir configured to contain a supply of product;

a nozzle to disperse the product, said nozzle being disposed at a point of dispersal;

an electrode to receive electrical power from a power supply and deliver electrical power to the product;

a channel disposed between said reservoir and said nozzle, wherein said channel permits the electrostatic charging of the product upon the product moving within said channel, wherein said charging of the moving product in said channel minimizes electrical contamination into said reservoir; and a continuous positive displacement mechanism adapted to move the product from the supply point to the dispersal point, wherein said displacement mechanism delivers the product in a substantially steady-state flow rate condition.

2. The disposable cartridge according to claim 1, further comprising an insulator, wherein said channel is disposed within said insulator.

3. The disposable cartridge according to claim 2, further comprising an aperture within said insulator, said aperture permits the product to be electrostatically charged.

4. The disposable cartridge according to claim 1, wherein a portion of said electrode is disposed between said reservoir and said nozzle.

5. The disposable cartridge according to claim 4, wherein said portion of said electrode is disposed closer to said nozzle than to said reservoir.

6. The disposable cartridge according to claim 1, wherein said electrode extends outwardly from the exterior surface of said cartridge.

7. The disposable cartridge according to claim 1, wherein said electrode is an annular contact.

8. The disposable cartridge according to claim 1, wherein said electrode is made of conductive plastic.

9. The disposable cartridge according to claim 1, wherein said electrode is made having carbon fibers.

10. The disposable cartridge according to claim 1, wherein said electrode aligns said disposable cartridge within the electrostatic spraying device.

11. The disposable cartridge according to claim 1, wherein said nozzle is made of a non-conductive material.

12. The disposable cartridge according to claim 2, wherein said nozzle, said electrode and said insulator together form a single integrated part.

13. A disposable cartridge for use in an electrostatic spraying device, said disposable cartridge comprising:

a reservoir configured to contain a supply of product;

a nozzle to disperse the product, said nozzle being disposed at the point of dispersal;

an electrode to receive electrical power from a power supply and deliver electrical power to the product;

a separate channel disposed between said reservoir and said nozzle, wherein an electrostatic charge is applied to the product within said channel and prior to contact of said product with said nozzle, wherein said channel permits the electrostatic charging of the product upon said product moving within said channel, wherein said charging of the moving product in said channel minimizes electrical contamination into said reservoir; and a continuous positive displacement mechanism adapted to move the product from the supply point to the dispersal point, wherein said displacement mechanism delivers the product in a substantially steady-state flow rate condition.

14. A disposable cartridge for use in an electrostatic spraying device, said disposable cartridge comprising:

a reservoir configured to contain the supply of product;

a nozzle to disperse the product, said nozzle being disposed at the point of dispersal;

a channel disposed between said reservoir and said nozzle, wherein said channel permits the electrostatic charging of the product upon said product moving within said channel, wherein said charging of the moving product in said channel minimizes electrical contamination into said reservoir;

an insulator, wherein said channel is disposed within said insulator;

an aperture within said insulator, said aperture permits the product to be electrostatically charged;

an electrode to receive electrical power from a power supply and deliver electrical power through said aperture to the product, wherein a portion of said electrode is disposed between said reservoir and said nozzle; and a continuous positive displacement mechanism adapted to move the product from the supply point to the dispersal point, wherein said displacement mechanism delivers the product in a substantially steady-state flow rate condition.

15. The disposable cartridge according to claim 14, wherein said electrode aligns said disposable cartridge within the electrostatic spraying device.

16. The disposable cartridge according to claim 14, wherein said portion of said electrode is disposed closer to said nozzle than to said reservoir.

17. The disposable cartridge according to claim 14, wherein said electrode extends outwardly from the exterior surface of said cartridge.

18. The disposable cartridge according to claim 14, wherein said electrode is an annular contact.

19. The disposable cartridge according to claim 14, wherein said electrode is made of conductive plastic having carbon fibers.

* * * * *

UNITED STATES PATENT AND TRADEMARK OFFICE

CERTIFICATE OF CORRECTION

PATENT NO. : 6,318,647 B1
DATED : November 20, 2001
INVENTOR(S) : Gaw et al.

It is certified that error appears in the above-identified patent and that said Letters Patent is hereby corrected as shown below:

Column 1,
Line 18, “produces” should read -- products --.

Column 3,
Line 27, “users” should read -- user’s --.

Column 5,
Line 31, “contacts” should read -- contact --.

Column 6,
Line 9, omit the word “a”.

Column 7,
Line 20, “96141]” should read -- 9614] --.
Line 22, “front” should read -- from --.

Column 8,
Line 26, omit the word “rife”.

Column 10,
Line 7, “on” should read -- one --.

Column 14,
Line 36, “Electrostatiic” should read -- Electrostatic --.

Signed and Sealed this

Thirtieth Day of September, 2003

JAMES E. ROGAN
*Director of the United States Patent and Trademark Office*